US011627913B2

(12) United States Patent
Ronen et al.

(10) Patent No.: US 11,627,913 B2
(45) Date of Patent: *Apr. 18, 2023

(54) IDENTIFICATION OF ORIENTATION OF IMPLANTED LEAD

(71) Applicant: Medtronic, Inc., Minneapolis, MN (US)

(72) Inventors: Shai Ronen, Louisville, CO (US); Andre D. A. Souza, Boylston, MA (US); Jiashu Li, Mounds View, MN (US); Patrick A. Helm, Milton, MA (US)

(73) Assignee: MEDTRONIC, INC., Minneapolis, MN (US)

( * ) Notice: Subject to any disclaimer, the term of this patent is extended or adjusted under 35 U.S.C. 154(b) by 1028 days.

This patent is subject to a terminal disclaimer.

(21) Appl. No.: 16/394,755

(22) Filed: Apr. 25, 2019

(65) Prior Publication Data

US 2020/0337637 A1    Oct. 29, 2020

(51) Int. Cl.
*A61B 5/00* (2006.01)
*A61B 90/00* (2016.01)
(Continued)

(52) U.S. Cl.
CPC ............ *A61B 5/4887* (2013.01); *A61B 90/39* (2016.02); *A61N 1/05* (2013.01); *A61N 1/3605* (2013.01);
(Continued)

(58) Field of Classification Search
CPC ........ A61B 5/4887; A61B 90/39; A61N 1/05; A61N 1/3605; A61N 1/36064; A61N 1/36067; A61N 1/36082; A61N 1/0534; G06T 7/0012; G06T 7/73; G06T 2207/10081; G06T 2207/20048; G06T 2207/30052; G06T 2207/30204; G06T 2207/10088; G06T 2207/10116; G06T 2207/10132; G06T 7/74; G06V 10/7715
See application file for complete search history.

(56) References Cited

U.S. PATENT DOCUMENTS 8,160,328 B2   4/2012   Goetz et al.
8,995,731 B2   3/2015   Joglekar
(Continued)

OTHER PUBLICATIONS

International Search Report and Written Opinion of International Application No. PCT/US2020/023698, dated Jun. 22, 2020, 14 pp.
(Continued)

*Primary Examiner* — John B Strege
(74) *Attorney, Agent, or Firm* — Shumaker & Sieffert, P.A.

(57) ABSTRACT

An example method includes obtaining an image of a lead implanted in a patient, the lead including one or more electrodes positioned along a longitudinal axis of the lead and a plurality of orientation markers; determining, in the image, respective locations of the electrodes and respective locations of the orientation markers; obtaining a template model corresponding to the lead; determining a transform between the determined locations of the one or more electrodes and the plurality of orientation markers and locations of corresponding electrodes and orientation markers in the template model; and determining the rotational orientation of the lead based on the transform.

20 Claims, 10 Drawing Sheets

(51) Int. Cl.
*G06T 7/73* (2017.01)
*A61N 1/05* (2006.01)
*A61N 1/36* (2006.01)
*G06T 7/00* (2017.01)
*G06V 10/77* (2022.01)

(52) U.S. Cl.
CPC .............. *G06T 7/0012* (2013.01); *G06T 7/73* (2017.01); *G06V 10/7715* (2022.01); *G06T 2207/10081* (2013.01); *G06T 2207/20048* (2013.01); *G06T 2207/30052* (2013.01); *G06T 2207/30204* (2013.01)

(56) References Cited

U.S. PATENT DOCUMENTS

| | | | |
|---|---|---|---|
| 9,308,372 | B2 | 4/2016 | Sparks et al. |
| 10,959,672 | B2 * | 3/2021 | Souza ................... A61N 1/05 |
| 2010/0135553 | A1 | 6/2010 | Joglekar |
| 2012/0071870 | A1 * | 3/2012 | Salahieh ............ A61B 1/00082 606/33 |
| 2013/0261684 | A1 | 10/2013 | Howard |
| 2017/0056678 | A1 * | 3/2017 | Bokil ....................... A61B 6/12 |
| 2017/0100593 | A1 | 4/2017 | Zottola |
| 2018/0104472 | A1 * | 4/2018 | Govea .................. A61N 1/3605 |
| 2018/0104482 | A1 * | 4/2018 | Bokil ..................... A61B 90/39 |
| 2018/0169415 | A1 * | 6/2018 | Seeley .................... A61B 5/291 |
| 2018/0296279 | A1 * | 10/2018 | Tyulmankov ...... A61B 17/3468 |
| 2020/0037942 | A1 * | 2/2020 | Howard ............... A61B 5/1127 |
| 2022/0061784 | A1 * | 3/2022 | Baxter, III ............... A61N 1/05 |
| 2022/0184401 | A1 * | 6/2022 | Vaidyanathan .... A61N 1/36139 |

OTHER PUBLICATIONS

U.S. Appl. No. 16/394,736, by Medtronic, Inc. (naming inventors: Souza et al.), filed Apr. 25, 2019.

International Preliminary Report on Patentability from International Application No. PCT/US2020/023698, dated Nov. 4, 2021, 6 pp.

* cited by examiner

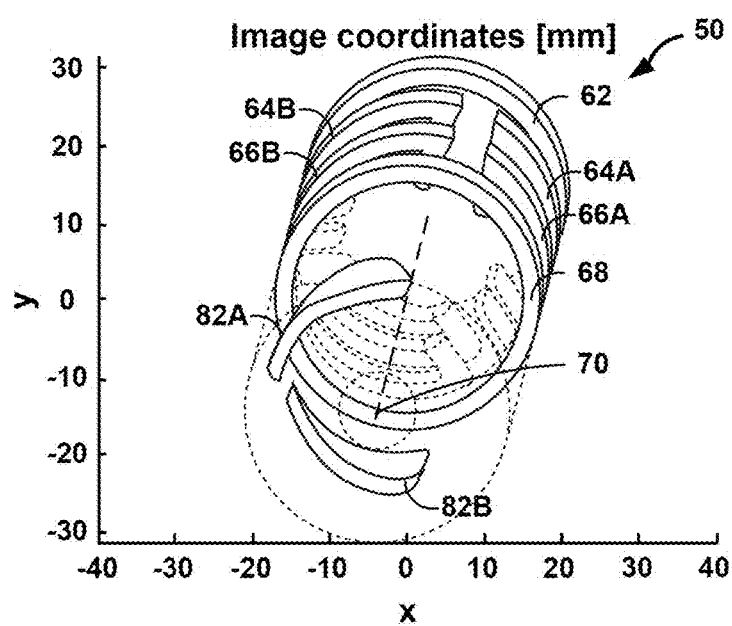
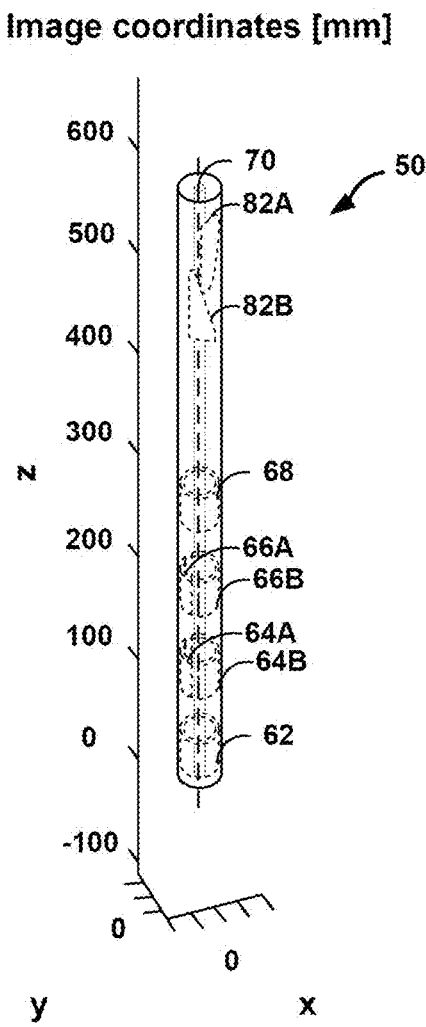
FIG. 7A
FIG. 7B

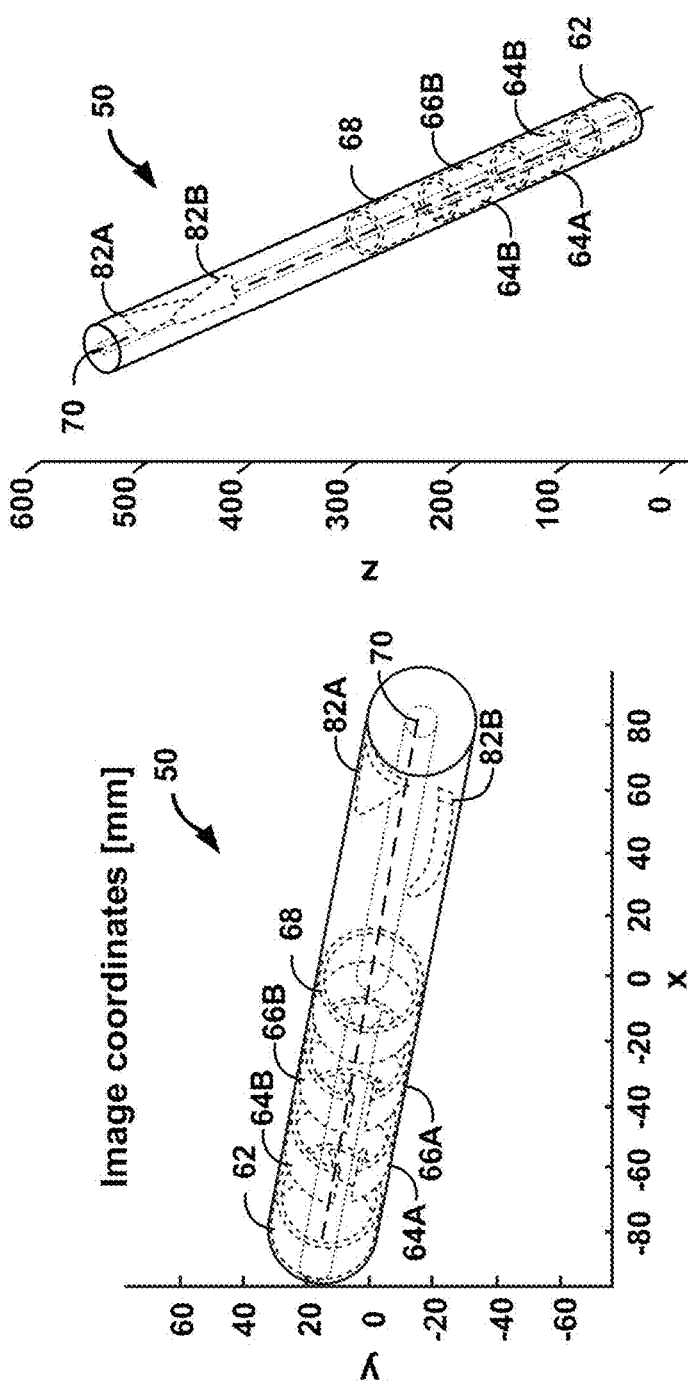
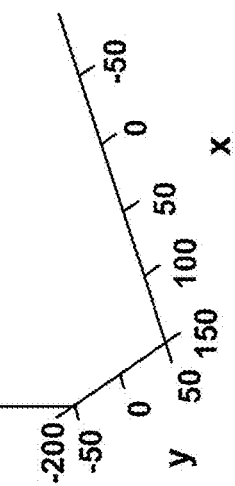
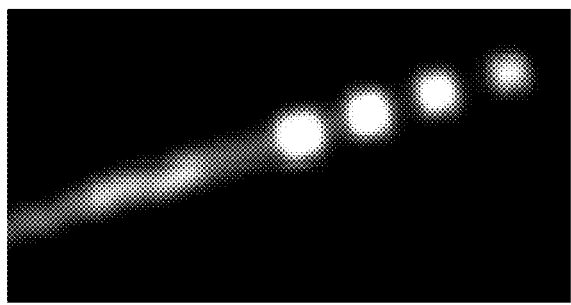
FIG. 8
FIG. 9A
FIG. 9B

IDENTIFICATION OF ORIENTATION OF IMPLANTED LEAD

TECHNICAL FIELD

The disclosure relates to electrical stimulation therapy.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some therapy systems, an implantable electrical stimulator delivers electrical therapy to a target tissue site within a patient with the aid of one or more electrodes, which may be deployed by medical leads and/or on a housing of the electrical stimulator, or both.

During a programming session, which may occur during implant of the medical device, during a trial session, or during an in-clinic or remote follow-up session after the medical device is implanted in the patient, a clinician may generate one or more therapy programs (also referred to as therapy parameter sets) that are found to provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in which electrical stimulation is delivered in the form of electrical pulses, for example, the therapy parameters may include an electrode configuration including an electrode combination and electrode polarities, an amplitude, which may be a current or voltage amplitude, a pulse width, and a pulse rate.

SUMMARY

In one example, a method includes obtaining an image of a lead implanted in a patient, the lead including one or more electrodes positioned along a longitudinal axis of the lead and a plurality of orientation markers; determining, in the image, respective locations of the electrodes and respective locations of the orientation markers; obtaining a template model corresponding to the lead; determining a transform between the determined locations of the one or more electrodes and the plurality of orientation markers and locations of corresponding electrodes and orientation markers in the template model; and determining the rotational orientation of the lead based on the transform.

In another example, a system includes a memory; and processing circuitry configured to: obtain an image of a lead implanted in a patient, the lead including one or more electrodes positioned along a longitudinal axis of the lead and a plurality of orientation markers; determine, in the image, respective locations of the electrodes and respective locations of the orientation markers; obtain a template model corresponding to the lead; determine a transform between the determined locations of the one or more electrodes and the plurality of orientation markers and locations of corresponding electrodes and orientation markers in the template model; and determine the rotational orientation of the lead based on the transform.

In another example, a computer-readable storage medium stores instructions that, when executed, cause one or more processors to: obtain an image of a lead implanted in a patient, the lead including one or more electrodes positioned along a longitudinal axis of the lead and a plurality of orientation markers; determine, in the image, respective locations of the electrodes and respective locations of the orientation markers; obtain a template model corresponding to the lead; determine a transform between the determined locations of the one or more electrodes and the plurality of orientation markers and locations of corresponding electrodes and orientation markers in the template model; and determine the rotational orientation of the lead based on the transform.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 7A and 7B are conceptual diagrams illustrating example visualizations of a lead, in accordance with one or more techniques of this disclosure.

FIG. 8 is an example image generated by an imaging device of an implanted lead in a patient, in accordance with one or more techniques of this disclosure.

FIGS. 9A and 9B are conceptual diagrams illustrating example visualizations of a lead, in accordance with one or more techniques of this disclosure.

DETAILED DESCRIPTION

Figure 1:
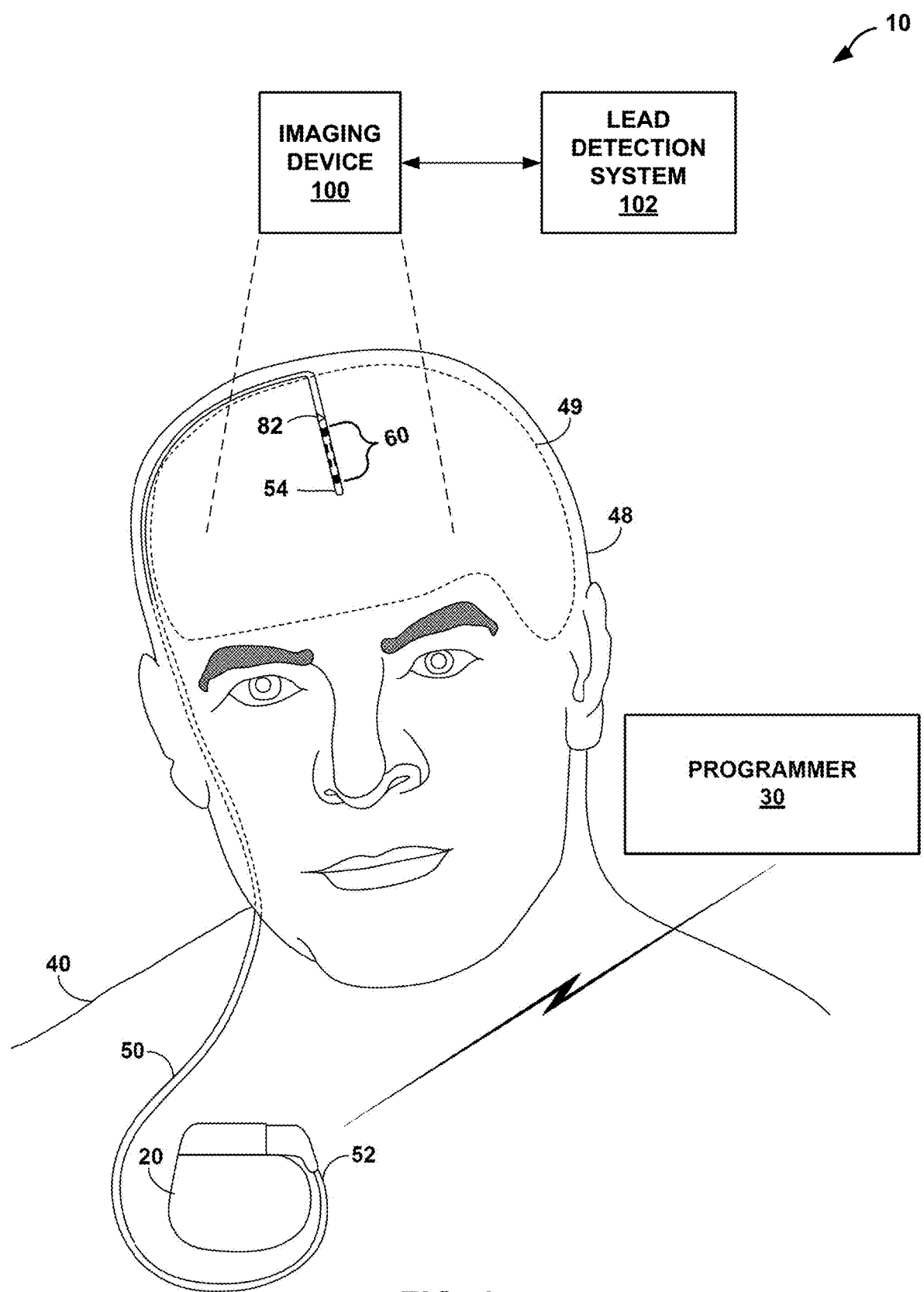
FIG. 1 is a conceptual diagram illustrating an example deep brain stimulation (DBS) system configured to detect a lead configured to deliver electrical stimulation therapy to a tissue site within a brain of a patient.

In general, the disclosure is directed to devices, systems, and methods for determining an orientation and/or position of a lead implanted in a patient. A lead may include one or more electrodes that are used to deliver electrical stimulation therapy to the patient. Some electrodes, such as ring electrodes disposed completed around a perimeter of a lead housing, may deliver electrical stimulation therapy radially in all directions about a longitudinal axis of the lead. Other electrodes, such as partial ring or segmented electrodes, may be directional electrode in that they enable the delivery of electrical stimulation therapy radially in only certain directions about the longitudinal axis of the lead that correspond with the position of the partial ring or segmented electrode. The rotational orientation of the lead (i.e., to enable the targeting of specific tissue) may facilitate programming a stimulator to deliver therapy using electrodes having complex geometry. However, a clinician may not be able to implant a lead with a specific rotational orientation and/or the leads may rotate about the longitudinal axis after initial insertion (e.g., upon securing the lead and/or over time being implanted within the patient).

In accordance with one or more techniques of this disclosure, a system may utilize images of a patient to determine an orientation and/or a location of a lead implanted in the patient. The lead may include various features to facilitate the determination of the lead orientation. For instance, the lead may include a plurality of orientation markers at specific positions. These orientation markers may be configured (e.g., shaped and/or made from certain materials) to be detectable in the image.

In operation, the system may obtain image data representing an image (e.g., a CT image) of at least the area of the patient in-which the lead is implanted (e.g., a head of the patient where the lead is implanted in a brain of the patient). The system may analyze the image data to determine the orientation and/or position of the lead. For instance, the system may identify respective locations of the electrodes and respective locations of the orientation markers.

The system may use any combination of a variety of techniques to determine the orientation and/or position of the lead based on the identified locations of the electrodes and the orientation markers. In a first technique, the system may determine an axis of this image based on the locations of the electrodes, generate a projected line between a first orientation marker and a second orientation marker in a plane orthogonal to the axis, and determine a rotational orientation of the lead based on an angle of the projected line. In a second technique, the system may match the locations of the electrodes and markers to a template model of the lead (e.g., using a singular value decomposition (SVD) based algorithm), and determine the orientation of the lead based on the match.

The system may provide the results (i.e., the predicted orientation and/or positions of the electrodes) to a practitioner (e.g., a physician, a physician's assistant, or other clinician). As one example, the system may output, for display, a graphical indication (e.g., a visualization) of the lead as-implanted. For instance, the system may output a graphical representation of the lead as-implanted overlaid on an image of the patient (e.g., the lead may be shown with respect to various anatomical landmarks). As another example, the system may output a differential angle that represents a difference between a target orientation and the determined orientation.

FIG. 1 is a conceptual diagram illustrating an exemplary therapy system 10 including lead 50 implanted in the brain 49 of patient 40. For ease of illustration, examples of the disclosure will primarily be described with regard to implantable electrical stimulation leads and implantable medical devices that apply neurostimulation therapy to brain 49 of patient 40 in the form of deep brain stimulation (DBS). However, the features and techniques described herein may be useful in other types of medical device systems which employ medical leads to deliver electricals stimulation to a patient and/or sense electrical signals via one or more electrodes of the lead. For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient. The medical lead system may be used with human subjects or with non-human subjects.

As shown in FIG. 1, therapy system 10 includes medical device programmer 30, implantable medical device (IMD) 20, and lead 50. Lead 50 includes plurality of electrodes 60, and plurality of orientation markers 82 adjacent a distal end 54 of lead 50. IMD 20 includes a stimulation therapy module that includes an electrical stimulation generator that generates and delivers electrical stimulation therapy to one or more regions of brain 49 of patient 40 via one or more of electrodes 60. In the example shown in FIG. 1, therapy system 10 may be referred to as a DBS system because IMD 20 provides electrical stimulation therapy directly to tissue within brain 49, e.g., a tissue site under the dura mater of brain 49. In other examples, one or more of lead 50 may be positioned to deliver therapy to a surface of brain 49 (e.g., the cortical surface of brain 49).

Lead 50 includes distal end 54 and a proximal end 52. As lead 50 is assembled, respective electrical connection sleeves (not shown in FIG. 1) adjacent proximal end 52 provide an electrical connection between IMD 20 and the conductive pathways of lead 50 running to electrodes 60 adjacent distal end 54 defined by the plurality of conductors of lead 50. Using the conductive pathways, IMD 20 may deliver electrical stimulation to patient 40 and/or sense electric signals of patient 40 using lead 50. While FIG. 1 illustrates proximal end of lead 50 connected directly to the header of IMD 20, in other examples, the proximal end of lead 50 may be connected to one or more lead extensions which are connected to the header of IMD 20 to electrically connect lead 50 to IMD 20.

In the example shown in FIG. 1, IMD 20 may be implanted within a subcutaneous pocket below the clavicle of patient 40. In other examples, IMD 20 may be implanted within other regions of patient 40, such as a subcutaneous pocket in the abdomen or buttocks of patient 40 or proximate the cranium 48 of patient 40. Proximal end 52 of lead 50 is coupled to IMD 20 via a connection sleeve block (also referred to as a header), which may include, for example, electrical contacts that electrically couple to respective electrical contacts at proximal end 52 of lead 50. The electrical contacts electrically couple the electrodes 60 carried by distal end 54 of lead 50. Lead 50 traverses from the implant site of IMD 20 within a chest cavity of patient 40, along the neck of patient 40 and through the cranium of patient 40 to access brain 49. Generally, IMD 20 is constructed of a biocompatible material that resists corrosion and degradation from bodily fluids. IMD 20 may comprise a hermetic housing to substantially enclose components, such as a processor, therapy module, and memory.

Lead 50 may be positioned to deliver electrical stimulation to one or more target tissue sites within brain 49 to manage patient symptoms associated with a disorder of patient 40. Lead 50 may be implanted to position electrodes 60 at desired locations of brain 49 through respective holes in cranium 48. Lead 50 may be placed at any location within brain 49 such that electrodes 60 are capable of providing electrical stimulation to target tissue sites within brain 49 during treatment. Although FIG. 1 illustrates system 10 as including a single lead 50 coupled to IMD 20, in some examples, system 10 may include more than one lead.

Lead 50 may deliver electrical stimulation via electrodes 60 to treat any number of neurological disorders or diseases in addition to movement disorders, such as seizure disorders or psychiatric disorders. Lead 50 may be implanted within a desired location of brain 49 via any suitable technique, such as through respective burr holes in a skull of patient 40 or through a common burr hole in the cranium 48. Lead 50 may be placed at any location within brain 49 such that electrodes 60 of lead 50 are capable of providing electrical stimulation to targeted tissue during treatment. In the examples shown in FIG. 1, electrodes 60 of lead 50 are shown as segmented electrodes and ring electrodes. Electrodes 60 of lead 50 may have a complex electrode array geometry that is capable of producing shaped electrical fields. In this manner, electrical stimulation may be directed to a specific direction from lead 50 to enhance therapy efficacy and reduce possible adverse side effects from stimulating a large volume of tissue.

IMD 20 may deliver electrical stimulation therapy to brain 49 of patient 40 according to one or more stimulation therapy programs. A therapy program may define one or more electrical stimulation parameter values for therapy generated and delivered from IMD 20 to brain 49 of patient 40. Where IMD 20 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 40, therapy system 10 monitors electrical signals, such as, e.g., one or more bioelectrical brain signals of patient 40. For example, IMD 20 may include a sensing module that senses bioelectrical brain signals within one or more regions of brain 49. In the example shown in FIG. 1, the signals generated by electrodes 60 are conducted to the sensing module within IMD 20 via conductors within lead 50, including one or more conductors within lead 50 between distal end 54 and proximal end 52 of lead 50.

Programmer 30 wirelessly communicates with IMD 20 as needed to provide or retrieve therapy information. Programmer 30 is an external computing device that the user, e.g., the clinician and/or patient 40, may use to communicate with IMD 20. For example, programmer 30 may be a clinician programmer that the clinician uses to communicate with IMD 20 and program one or more therapy programs for IMD 20. Alternatively, programmer 30 may be a patient programmer that allows patient 40 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 20.

Programmer 30 may be a hand-held computing device with a display viewable by the user and an interface for providing input to programmer 30 (i.e., a user input mechanism). In other examples, programmer 30 may be a larger workstation or a separate application within another multi-function device, rather than a dedicated computing device. For example, the multi-function device may be a notebook computer, tablet computer, workstation, cellular phone, personal digital assistant, or another computing device that may run an application that enables the computing device to operate as a secure medical device programmer 30.

Again, while lead 50 is described here for use in DBS applications, lead 50 or other leads may be implanted at any other location within patient 40. For example, lead 50 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 40 and adjacent to sensitive nerve tissue. Therapy may also be changed if leads migrate to new locations within the tissue or patient 40 no longer perceives therapeutic effects of the stimulation. The features or techniques of this disclosure may be useful in other types of medical applications.

Figure 2:
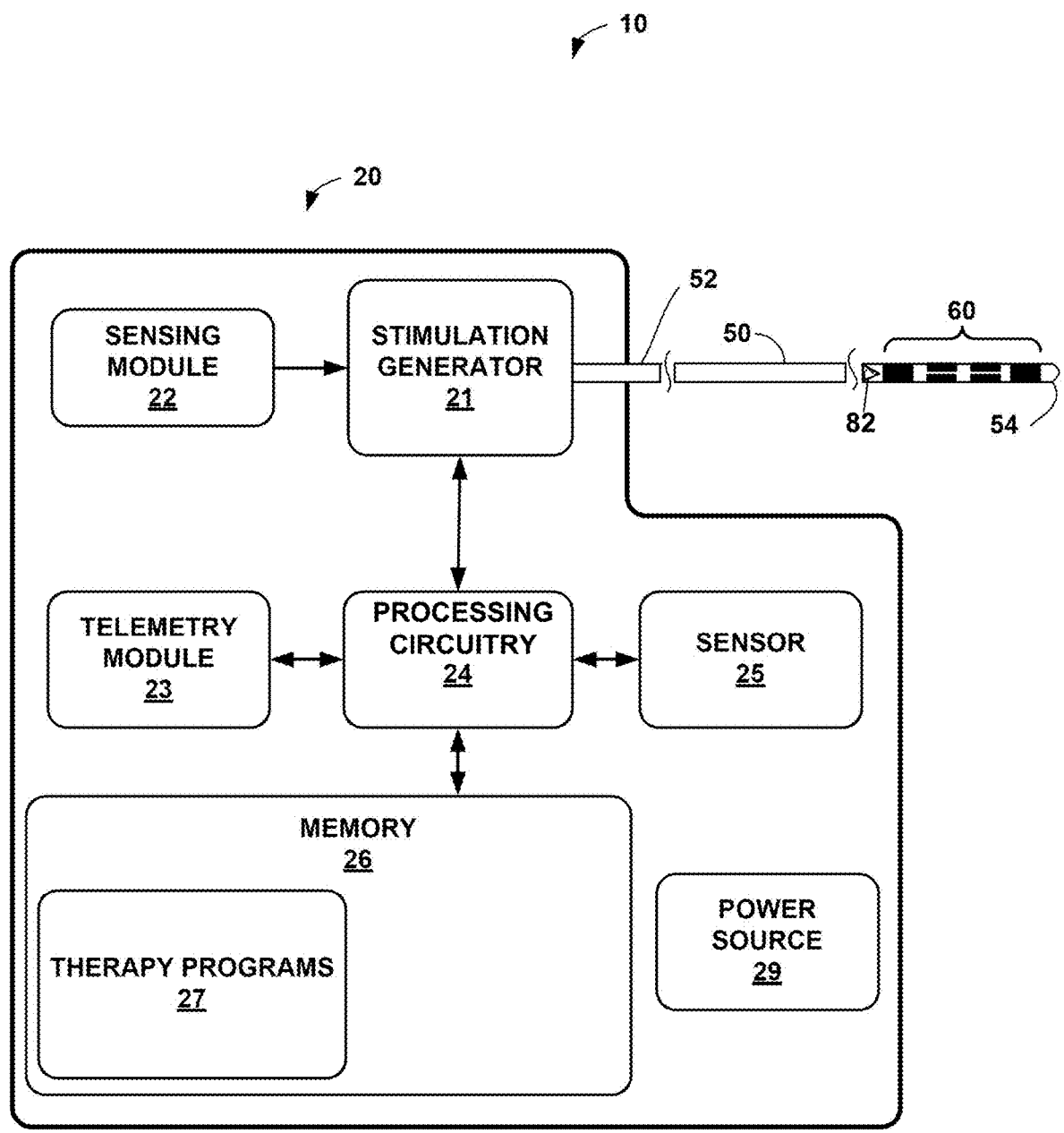
FIG. 2 is functional block diagram illustrating components of an example medical device.

FIG. 2 is a functional block diagram illustrating components of IMD 20. As shown, therapy system 10 includes IMD 20 coupled to lead 50. In the example of FIG. 2, IMD 20 includes processor circuitry 24 (also referred to as "processor", "processors", or "processing circuitry"), memory 26, stimulation generator 21, sensing module 22, telemetry module 23, sensor 25, and power source 29. Each of these components (also referred to as "modules" may be or include electrical circuitry configured to perform the functions attributed to each respective module). For example, processor 24 may include processing circuitry, stimulation generator 21 may include switch circuitry, sensing module 22 may include sensing circuitry, and telemetry module 23 may include telemetry circuitry. Memory 26 may include any volatile or non-volatile media, such as a random-access memory (RAM), read only memory (ROM), non-volatile RAM (NVRAM), electrically erasable programmable ROM (EEPROM), flash memory, and the like. Memory 26 may store computer-readable instructions that, when executed by processor 24, cause IMD 20 to perform various functions. Memory 26 may be a storage device or other non-transitory medium.

Processor 24 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 24 herein may be embodied as firmware, hardware, software or any combination thereof. Processor 24 controls stimulation generator 21 to apply particular stimulation parameter values, such as amplitude, pulse width, and pulse rate.

In the example shown in FIG. 2, lead 50 includes electrodes 60 located at distal end 54. Processor 24 also controls stimulation generator 21 to generate and apply the stimulation signals to selected combinations of electrodes of the electrode module. In some examples, stimulation generator 21 includes a switch module that couples stimulation signals to selected conductors within lead 50, which, in turn, delivers the stimulation signals across selected electrodes. Such a switch module may be a switch array, switch matrix, multiplexer, or any other type of switching module configured to selectively couple stimulation energy to selected electrodes and to selectively sense bioelectrical neural signals of the spine with selected electrodes.

In other examples, however, stimulation generator 21 does not include a switch module. In these examples, stimulation generator 21 comprises a plurality of pairs of voltage sources, current sources, voltage sinks, or current sinks connected to each of electrodes such that each pair of electrodes has a unique signal generator. In other words, in these examples, each of electrodes is independently controlled via its own signal generator (e.g., via a combination of a regulated voltage source and sink or regulated current source and sink), as opposed to switching signals between electrodes.

Stimulation generator 21 may be a single channel or multi-channel stimulation generator. In particular, stimulation generator 21 may be capable of delivering a single stimulation pulse or multiple stimulation pulses at a given time via a single electrode combination or multiple stimulation pulses at a given time via multiple electrode combinations. In some examples, however, stimulation generator 21 may be configured to deliver multiple channels on a time-interleaved basis. For example, a switch module of stimulation generator 21 may serve to time divide the output of stimulation generator 21 across different electrode combinations at different times to deliver multiple programs or channels of stimulation energy to patient 40. In another example, the stimulation generator 21 may control the independent sources or sinks on a time-interleaved bases.

Figure 3:
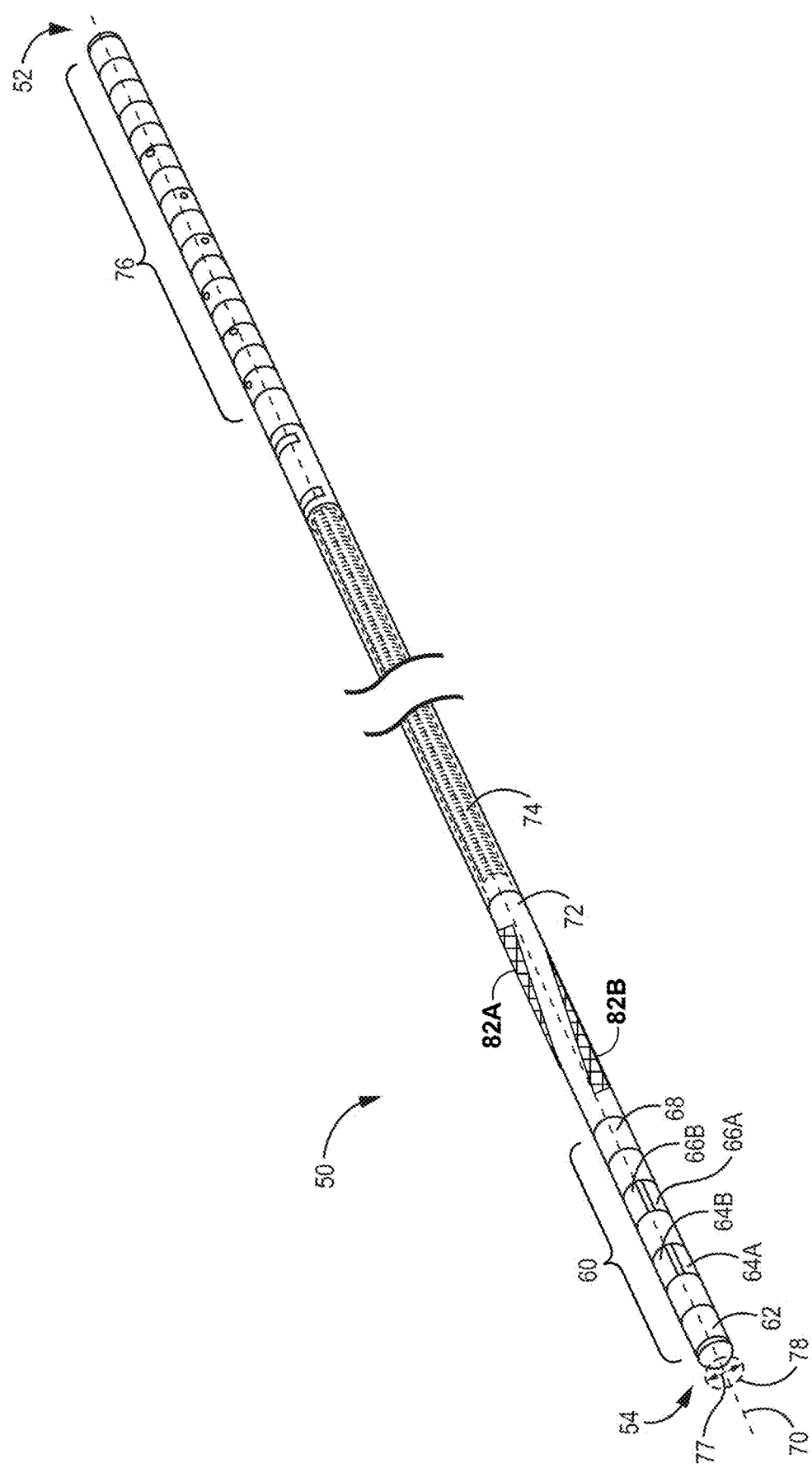
FIG. 3 is a conceptual diagram illustrating components of an example medical lead.

Lead 50 may include distal end 54 including a complex electrode array geometry (e.g., with one or more segmented electrodes along the longitudinal axis), but may also include one or more single ring electrodes along the longitudinal axis in other examples. It will be understood that "along the longitudinal axis" as used herein refers to an axial position along the length of the longitudinal axis that may be displaced radially from that axis. In one example, distal end 54 of lead 50 includes a plurality of electrodes 60 positioned at different axial positions along the longitudinal axis of the lead and a plurality of electrodes 60 positioned at different angular positions around the circumference of the lead/ around the longitudinal axis (which may be referred to as electrode segments). In this manner, electrodes may be selected along the longitudinal axis of lead 50 and along the circumference of the lead. Selectively activating electrodes 60 of lead 50 can produce customizable stimulation fields that may be directed to a particular side of lead 50 in order to isolate the stimulation field around the target anatomical region of brain 49. In the example of FIG. 3, lead 50 includes two ring electrodes 68, 62 with two segmented electrode rings 64, 66 each having three segmented electrodes (e.g., segmented electrodes 64A, 64B, 66A, 66B shown in FIG. 3) in between the respective electrodes 68, 62. The techniques described herein may be applied to leads having more or fewer segmented electrodes within a segmented electrode ring and/or to leads having more or fewer than two segmented electrode rings. These techniques may also be applied to leads having more or fewer than two ring electrodes. In yet other cases, lead 50 may include only segmented electrodes or only ring electrodes. In some examples, lead 50 may include a tip electrode which may be in the shape of a rounded cone or other shape that resides at the distal tip of lead 50.

Although sensing module 22 is incorporated into a common housing with stimulation generator 21 and processor 24 in FIG. 2, in other examples, sensing module 22 may be in a separate housing from IMD 20 and may communicate with processor 24 via wired or wireless communication techniques. Example bioelectrical signals include, but are not limited to, a signal generated from local field potentials within one or more regions of the spine or brain, for example.

Sensor 25 may include one or more sensing elements that sense values of a respective patient parameter. For example, sensor 25 may include one or more accelerometers, optical sensors, chemical sensors, temperature sensors, pressure sensors, or any other types of sensors. Sensor 25 may output patient parameter values that may be used as feedback to control delivery of therapy. IMD 20 may include additional sensors within the housing of IMD 20 and/or coupled as a separate module via one of lead 50 or other leads. In addition, IMD 20 may receive sensor signals wirelessly from remote sensors via telemetry module 23, for example. In some examples, one or more of these remote sensors may be external to patient (e.g., carried on the external surface of the skin, attached to clothing, or otherwise positioned external to the patient).

Telemetry module 23 supports wireless communication between IMD 20 and an external programmer (e.g., such as programmer 30) or another computing device under the control of processor 24. Processor 24 of IMD 20 may receive, as updates to programs, values for various stimulation parameters such as amplitude and electrode combination, from programmer 30 via telemetry module 23. The updates to the therapy programs may be stored within therapy programs 27 portion of memory 26. Telemetry module 23 in IMD 20, as well as telemetry modules in other devices and systems described herein, such as programmer 30, may accomplish communication by radiofrequency (RF) communication techniques. In addition, telemetry module 23 may communicate with external medical device programmer 30 via proximal inductive interaction of IMD 20 with programmer 30. Accordingly, telemetry module 23 may send information to programmer 30 on a continuous basis, at periodic intervals, or upon request from IMD 20 or programmer 30.

Power source 29 delivers operating power to various components of IMD 20. Power source 29 may include a small rechargeable or non-rechargeable battery and a power generation circuit to produce the operating power. Recharging may be accomplished through proximal inductive interaction between an external charger and an inductive charging coil within IMD 20. In some examples, power requirements may be small enough to allow IMD 20 to utilize patient motion and implement a kinetic energy-scavenging device to trickle charge a rechargeable battery. In other examples, traditional batteries may be used for a limited period of time.

FIG. 3 is a conceptual diagram illustrating an example medical lead 50. In the example of FIG. 3, there are eight conductors corresponding to eight respective electrodes—2 ring electrodes and 6 segmented electrodes—and eight electrical terminals, such that the lead 50 defines eight isolated electrical paths or channels for delivery of therapy and/or sensing of electrical signals by IMD 20. However, in other examples, greater or fewer conductors, electrodes, and terminals may be used. Lead 50 includes a distal end 54 and a proximal end 52, corresponding to an electrode end and a terminal end, respectively. Distal end 54 and proximal end 52 may define a longitudinal axis 70 along a length of lead 50. Lead 50 includes an outer perimeter 78 that has a diameter 77. In some examples, diameter 77 of outer perimeter 78 may be between approximately 25 millionth of an inch (mils) and 100 mils, although other values are contemplated.

Lead 50 may include a lead body 72 extending between distal end 54 and proximal end 52. Lead body 72 may be configured to provide structure and support to lead 50 and to encase at least a portion of a plurality of conductors 74. At least a portion of lead body 72 may include conductors in a coiled arrangement. In some examples, lead body 72 may act as an insulator between the plurality of conductors 74. In some examples, lead body 72 may extend through the length of lead 50 as a monolithic form. Lead body 72 may be formed from a polymeric material including, but not limited to, polyurethanes, silicones, fluoropolymers, fluoroelastomers, polyethylenes, polyesters, and other biocompatible polymers suitable for contact with bodily tissue.

Lead 50 may include a plurality of terminals 76 near proximal end 52. Each terminal of the plurality of terminals 76 may be configured to electrically couple to a conductor 74 within lead body 72 of lead 50 and a conductor external of lead 50, such as a contact of IMD 20 of FIG. 1. The plurality of terminals 76 may be positioned at or near proximal end 52 of lead 50. In some examples, each terminal in the plurality of terminals 76 may be a ring contact that extends around outer perimeter 78 of lead 50.

Lead 50 may include the plurality of electrical conductors 74 extending about longitudinal axis 70 of lead 50. The plurality of electrical conductors 74 may be electrically isolated from one another by lead body 72 to form separate channels, circuits, or conductive paths through the lead body 72 although techniques described herein also apply to lead body 72 carrying a single conductor. As shown in FIG. 3, the plurality of conductors 74 may be in a coiled arrangement for at least a portion of lead 50 (e.g., between the electrodes 60 and terminal terminals 76). The coiled arrangement of the plurality of conductors 74 may by wound around longitudinal axis 70 of lead 50. In some examples, the plurality of electrical conductors 74 may include an electrical insulator sheath around a conductive portion. The electrical insulator sheath may be configured to electrically insulate a conductor 74 from undesired contact with an electrode or terminal for which electrical contact is not intended for the conductor 74. In some examples, each of the plurality of electrical conductors 74 may have a diameter, with or without the electrical insulator sheath, between at least approximately 0.0025 in. and approximately 0.0080 in.

Each of the plurality of electrical conductors 74 may have a distal connection portion on a distal end and a proximal connection portion on a proximal end of each conductor. The distal and proximal connection portions may be configured to electrically couple each of the plurality of electrical conductors 74 to a respective electrode of the plurality of electrodes 60 and a respective terminal of the plurality of terminals 76. In some examples, the distal and proximal connection portions may include connections sleeves around a perimeter of the respective conductor, where a diameter of each connection sleeve may be larger, smaller, or the same size as a diameter of the remainder conductor body of the respective conductor. In some examples, such as for conductors having an electrical insulator sheath described above, the plurality of conductors 74 may not have distal or proximal connection portions that include connection sleeves. For example, a distal portion of the electrical insulator sheath of a conductor may be removed to expose bare metal conductor. This bare metal conductor may operate as the distal connection portion to electrically contact an electrode or terminal. Each of the plurality of electrodes 60 may be formed from an electrically conductive material including, but not limited to, platinum, palladium, iridium, titanium and titanium alloys such as titanium molybdenum alloy (TiMoly), nickel and nickel alloys such as MP35N alloy, and the like. For example, electrodes may be formed from an 80/20 platinum/iridium alloy suitable for mechanical crimping.

Lead 50 may include a plurality of electrodes 60 near distal end 54. In the example of FIG. 3, the plurality of electrodes 60 includes ring electrodes 62 and 68, and segmented electrodes, such as segmented electrodes 64A, 64B, 66A, and 66B. While only segmented electrodes 64A, 64B, 66A, and 66B are shown, the segmented electrodes may form a discontinuous conductive ring that includes a plurality of electrodes, such as 64A, 64B, and an anterior electrode 64C (not shown) for an exemplary ring of three segmented electrodes on one ring (collectively referred to as "segmented electrode ring 64"), and 66A, 66B, and an anterior electrode 66C (not shown) on another ring (collectively referred to as "segmented electrode ring 66"). Each segmented electrode of a respective discontinuous segmented electrode ring is electrically isolated from the other segmented electrodes in the respective discontinuous segmented electrode ring. For example, segmented electrodes 64A and 64B, which are part of discontinuous segmented electrode ring 64, are electrically isolated from each other. In this example, there are two sets of three segmented electrodes forming segmented electrode rings 64 and 66 at distal end 54 of lead 50, such that each set of segmented electrodes forming segmented electrode rings 64 and 66 is aligned along a longitudinal axis of the electrode module and the sets are positioned circumferentially around outer perimeter 78 of lead 50. In other examples, one or more segmented electrodes may be positioned along the longitudinal axis without being symmetrically arranged around the longitudinal axis. For instance, a single segment spanning between 90 and 120 degrees may be the only electrode at a particular axial location along the length of the lead such that there is not radial symmetry.

The plurality of electrodes 60 of lead 50 may be constructed of a variety of different designs. For example, one or more leads 50 may include two or more electrodes at each longitudinal location along the length of the lead, such as multiple electrodes at different perimeter locations around outer perimeter 78 of lead 50 at each of the locations, such as by using electrode modules. As mentioned above, each electrode of the plurality of electrodes 60 may be electrically coupled to a respective electrical conductor of the plurality of electrical conductors 74. Each of the plurality of electrodes 60 may be formed from a biocompatible electrically conductive material including, but not limited to, platinum, palladium, iridium, and other biocompatible materials suitable for contact with bodily tissue. For example, electrodes may be formed from a 90/10 platinum/iridium alloy.

Referring to FIGS. 1-3, as discussed above, in some examples, it may be desirable for a clinician to be aware of the orientation and/or position of lead 50. For instance, it may be desirable for a clinician to be aware of the orientation and/or position of lead 50 when using programmer 30 to program IMD 20 to deliver electrical stimulation to patient 40 via electrodes 60 of lead 50.

In accordance with one or more techniques of this disclosure, therapy system 10 may include lead detection system 102, which may be configured to determine an orientation and/or a location of lead 50 as implanted in patient 40. As shown in FIG. 1, lead detection system 102 may determine the orientation and/or the location of lead 50 based on image data captured by imaging device 100.

Imaging device 100 may represent any device capable of capturing images of a patient. Examples of imaging device 100 include, but are not necessarily limited to, x-ray imaging devices, computed tomography (CT) imaging devices, magnetic resonance imaging (MRI) devices, ultrasound imaging devices, and any other type of imaging device. In one specific example imaging device 100 includes the O-Arm™ imaging system available from Medtronic Inc. In some examples, imaging device 100 may be capable of producing image data with a resolution at least (1.0 mm×1.0 mm×1.0 mm), (0.6 mm×0.6 mm×0.6 mm), (0.4 mm×0.4 mm×0.4 mm), . . . , (0.1 mm×0.1 mm×0.1 mm), or any other resolution suitable for imaging lead 50.

Imaging device 100 may provide image data corresponding to the captured image to other components of system 10, such as lead detection system 102. Imaging device 100 may provide the image data in any suitable format. Example formats include, but are not necessarily limited to, Analyze, Neuroimaging Informatics Technology Initiative (Nifti), Minc, and Digital Imaging and Communications in Medicine (Dicom).

Lead detection system 102 may represent a system configured to analyze image data to determine an orientation and/or a location of a lead implanted in a patient. In the example of FIG. 1, lead detection system 102 may analyze image data generated by imaging device 100 to determine an orientation and/or a location of lead 50 after lead 50 has been implanted in patient 40.

Lead 50 may include various features to facilitate lead detection system 102 in determining the orientation and/or the location. For instance, as shown in the example of FIG. 3, lead 50 may include orientation markers 82A and 82B (collectively, "orientation markers 82"). Orientation markers 82 may be located at specific positions within lead 50 relative to positions of electrodes 60 such that the rotational orientation of orientation markers 82 is a function of the rotational orientation of electrodes 60. Additionally, in some examples, orientation makers 82 may be positioned at a specific distance, or distances, along longitudinal axis 70 from one or more of electrodes 60. For instance, orientation makers 82 may be positioned at a specific distance along longitudinal axis 70 from the most distal electrode (i.e., electrode 62 in FIG. 3).

In some examples, orientation markers 82 may be positioned at different positions along longitudinal axis 70. For instance, as shown in FIG. 3, orientation marker 82A may be positioned closer to a tip of distal end 54 than orientation marker 82B. As such, in some examples, orientation marker 82A may be referred to as an upper orientation marker and orientation marker 82B may be referred to as a bottom or lower orientation marker. As described below, positioning orientation markers 82 at different positions along longitudinal axis 70 enables lead detection system 102 to determine a specific rotational orientation of lead 50 (i.e., as opposed to determining two possible rotational orientations that are 180 degrees apart).

Orientation markers 82 may be formed from a material visible in images captured by imaging device 100. For instance, orientation markers 82 may be formed to include a radiopaque material such as at least one of barium sulfate, bismuth compounds, or tungsten. Orientation markers 82 may be formed in shapes to enable determination of the rotational orientation of lead 50. Example shapes include, but are not necessarily limited to, triangles, rectangles with windows, or the like.

Figure 4:
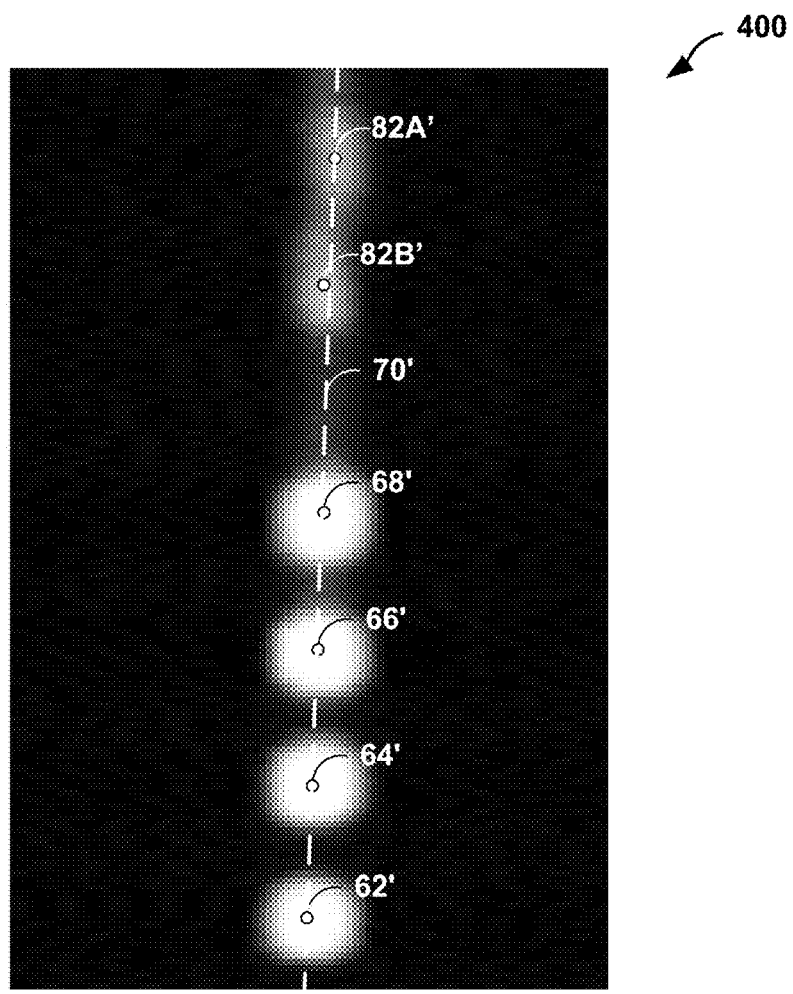
FIG. 4 is an example image generated by an imaging device of an implanted lead in a patient, in accordance with one or more techniques of this disclosure.

In operation, lead detection system 102 may receive (e.g., from imaging device 100) image data that represents an image of patient 40 after lead 50 has been implanted in patient 40. FIG. 4 is an example of an image generated by imaging device 100 that includes lead 50, or at least visible components of lead 50, in accordance with one or more techniques of this disclosure. As shown in FIG. 4, image 400 may correspond to an image of lead 50 of FIG. 3 implanted in patient 40.

Lead detection system 102 may also receive, determine, or otherwise obtain one or more parameters of lead 50. As one example, lead detection system 102 may receive user input indicating a manufacturer and model of lead 50. Based on the manufacturer and model of lead 50, lead detection system 102 may obtain (e.g., from a lead database, such as lead parameters 150 of FIG. 6) various parameters of lead 50, such as a number of electrodes on the lead, distances between orientation markers 82 and electrodes 60, angles between a vector connecting orientation markers 82 and centers (e.g., centroids) of electrodes 60, or any other parameters. As another example, lead detection system 102 may receive user input indicating the various parameters of lead 50, such as distances between orientation markers 82 and electrodes 60, angles between a vector connecting orientation markers 82 and centers of electrodes 60, or any other parameters.

Lead detection system 102 may analyze the image data to determine the orientation and/or position of lead 50. For instance, lead detection system 102 may identify respective locations (e.g., centroids) of electrodes 60 and respective locations of orientation markers 82. As shown in FIG. 4, lead detection system 102 may identify centroid 82A' of orientation marker 82A, centroid 82B' of orientation marker 82B, centroid 62' of electrode 62, centroid 64' of electrode 64, centroid 66' of electrode 66, and centroid 68' of electrode 68 (segmented electrodes 64A and 64B are aggregated into a single electrode in image 400 having centroid 64', and segmented electrodes 66A and 66B are aggregated into a single electrode in image 400 having centroid 66').

Lead detection system 102 may use any combination of a variety of techniques to determine the orientation and/or position of lead 50 based on the identified locations of electrodes 60 and orientation markers 82. In a first technique, lead detection system 102 may determine an axis of electrode 50 based on the locations of electrodes 60. For instance, lead detection system 102 may determine an orientation of longitudinal axis 70' that corresponds to longitudinal axis 70 of FIG. 3 (e.g., determine parameters of a vector that corresponds to longitudinal axis 70'). Lead detection system 102 may determine a plane orthogonal to the determined axis, and project the locations of orientation markers 82 into the determined plane.

Figure 5:
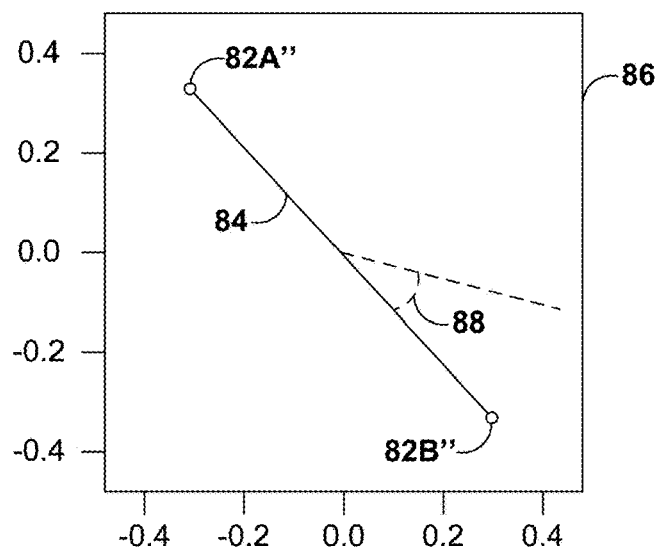
FIG. 5 is a conceptual diagram illustrating an example projection of locations of orientation markers into a plane orthogonal to an axis of a lead, in accordance with one or more techniques of this disclosure.

FIG. 5 is a conceptual diagram illustrating a projection of locations of orientation markers into a plane orthogonal to a longitudinal axis of a lead, in accordance with one or more techniques of this disclosure. As shown in FIG. 5, lead detection system 102 may determine plane 86 as a plane orthogonal to longitudinal axis 70' (FIG. 4), and project the locations of centroids 82A' and 82B' (respectively corresponding to the locations of orientation markers 82A and 82B) into plane 86 as projected centroids 82A" and 82B". In FIG. 5, the point located at (0.0, 0.0) may correspond to a point along longitudinal axis 70'.

Lead detection system 102 may determine the rotational orientation of lead 50 based on projected centroids 82A" and 82B". For instance, lead detection system 102 may calculate vector 84 that connects projected centroids 82A" and 82B" in plane 86. Vector 84 may represent the rotational orientation of orientation markers 82, and thus the rotational orientation of lead 50.

Additionally, as discussed above, orientation markers 82 may be located at specific positions within lead 50 relative to positions of electrodes 60 such that the rotational orientation of orientation markers 82 is a function of the rotational orientation of electrodes 60. Therefore, as vector 84 represents the rotational orientation of orientation markers 82, lead detection system 102 may determine the rotational orientation of electrodes 60 based on vector 84. For instance, based on information about lead 50 (e.g., a model number) lead detection system 102 may obtain angular offsets between vector 84 and centers of electrodes of electrodes 60. As one specific example, lead detection system 102 may obtain an angular offset 88 that represents the angle between a center (e.g., centroid) of electrode segment 64A and vector 84. Based on the obtained angular offsets, lead detection system 102 may determine vectors from the centers of one or more of electrodes 60.

In a second technique for determining the orientation and/or position of lead 50 based on the identified locations of electrodes 60 and orientation markers 82, lead detection system 102 may obtain a pre-determined template of expected centroids of electrodes 60 and orientation markers 82. The pre-determined template may be in a fixed, lead based, coordinate system. The template may represent size, shape, and/or radial and longitudinal spacing of the electrodes, and may further represent size, shape, and/or radial and longitudinal spacing of markers. The template may be referred to as a template model. Lead detection system 102 may determine a transform between the centroids determined from the image and the centroids in the template. For instance, lead detection system 102 may use singular value decomposition (SVD) to determine a best fit rigid transform between the centroids in the template and corresponding centroids 82A', 82B', 62', 64', 66', and 68'. Based on the determined transform, lead detection system 102 may determine the orientation of lead 50. Any type of transform may be used that can express the spatial relationship between the two sets of centroids.

In some examples, lead detection system 102 may use one of the first technique or the second technique to determine the orientation of lead 50. In other examples, lead detection system 102 may use a combination of the first technique and the second technique to determine the orientation of lead 50. For instance, lead orientation system 102 may use one of the first technique or the second technique to determine the orientation or lead 50 and use the other of the first technique or the second technique to confirm the determined orientation.

Figure 6A:
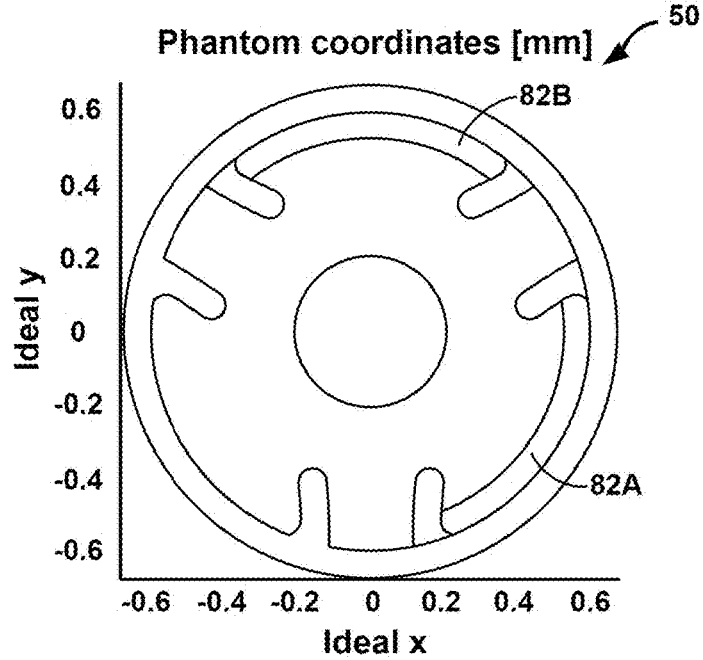
FIGS. 6A and 6B are conceptual diagrams illustrating example models of a lead, in accordance with one or more techniques of this disclosure.
Figure 6B:
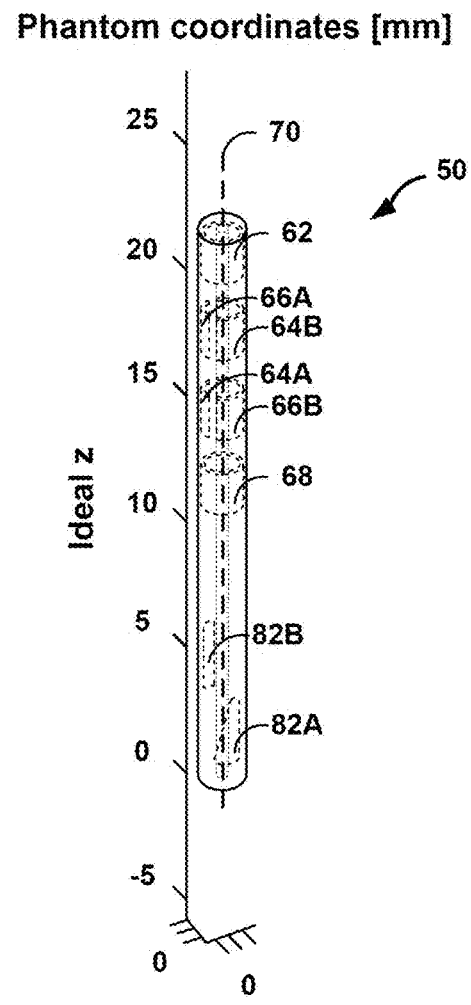

FIGS. 6A and 6B are conceptual diagrams illustrating example models of a lead, in accordance with one or more techniques of this disclosure. FIG. 6A shows an example two-dimensional model of lead 50 in a plane orthogonal to a longitudinal axis 70. FIG. 6B shows an example three-dimensional model of lead 50. The models shown in FIGS. 6A and 6B may be in a phantom coordinate system.

FIGS. 7A and 7B are conceptual diagrams illustrating example visualizations of a lead, in accordance with one or more techniques of this disclosure. FIG. 7A shows an example visualization of lead 50 in a x-y plane. FIG. 7B shows an example visualization of lead 50 after rotation of longitudinal axis 70 along the z-axis. The visualizations of FIGS. 7A and 7B may correspond to the image shown in FIG. 4.

As discussed herein, a system may determine an orientation of a lead based on an image of the lead as implanted in a patient. For instance, lead detection system 102 may process the image shown in FIG. 4 to determine the orientation of lead 50. The image shown in FIG. 4 may represent the data that lead detection system 102 actually receives, while the visualizations of FIGS. 7A and 7B may represent the concepts. Additionally, as discussed above, lead detection system 102 may determine the rotational orientation by determining a transform between features of a model of a lead and features of an image of the lead. In the example of FIGS. 7A and 7B, lead detection system 102 may determine that the transform between the model of FIGS. 6A and 6B and lead 50 is a roll of 177.96°, a pitch of 2.32°, and a yaw of −145.64°.

FIG. 8 is an example image generated by an imaging device of an implanted lead in a patient, in accordance with one or more techniques of this disclosure. The image of FIG. 8 is similar to the image of FIG. 4 (e.g., of an identical lead), however the lead in the image is tilted.

FIGS. 9A and 9B are conceptual diagrams illustrating example visualizations of a lead, in accordance with one or more techniques of this disclosure. FIG. 9A shows an example visualization of lead 50 in a x-y plane. FIG. 9B shows an example visualization of lead 50 after rotation of longitudinal axis 70 along the z-axis. The visualizations of FIGS. 9A and 9B may correspond to the image shown in FIG. 8.

As discussed herein, a system may determine an orientation of a lead based on an image of the lead as implanted in a patient. For instance, lead detection system 102 may process the image shown in FIG. 8 to determine the orientation of lead 50. The image shown in FIG. 8 may represent the data that lead detection system 102 actually receives, while the visualizations of FIGS. 9A and 9B may represent the concepts. Additionally, as discussed above, lead detection system 102 may determine the rotational orientation by determining a transform between features of a model of a lead and features of an image of the lead. In the example of FIGS. 9A and 9B, lead detection system 102 may determine that the transform between the model of FIGS. 6A and 6B and lead 50 is a roll of 167.39°, a pitch of −11.81°, and a yaw of −142-78°.

Figure 10:
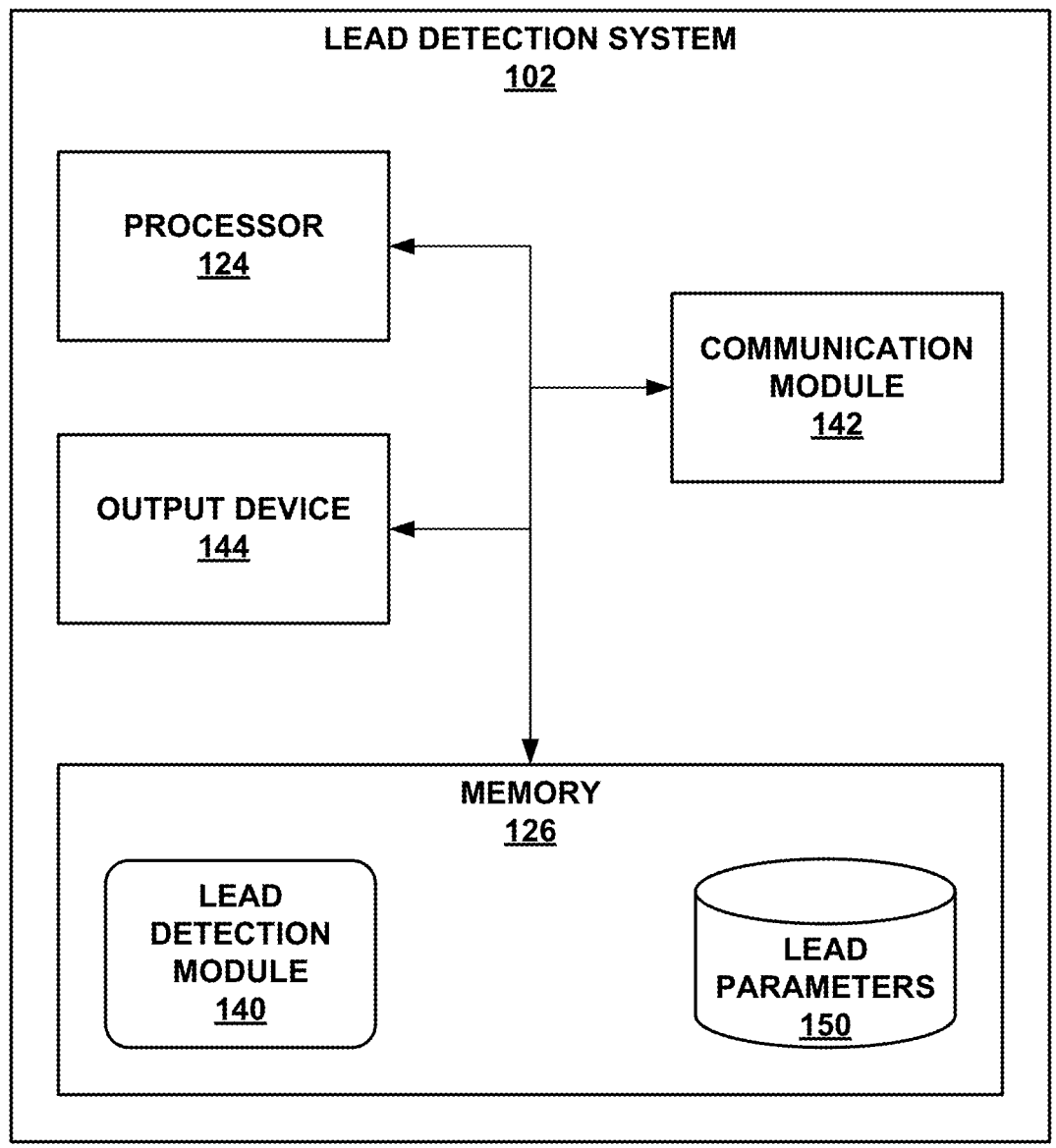
FIG. 10 is functional block diagram illustrating components of an example lead detection system.

FIG. 10 is a functional block diagram illustrating components of lead detection system 102. Examples of lead detection system 102 include, but are not necessarily limited to, desktops, tablets, laptops, mainframes, cloud computing environments, servers, or any type of other computing system. As one specific example, lead detection system 102 may be the StealthStation™ S8, available from Medtronic Inc. In the example of FIG. 10, lead detection system 102 includes processor circuitry 124 (also referred to as "processor"), memory 126, and communication module 128. Each of these components (also referred to as "modules" may be or include electrical circuitry configured to perform the functions attributed to each respective module).

Processor 124 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 124 herein may be embodied as firmware, hardware, software or any combination thereof.

Memory 126 may include any volatile or non-volatile media, such as a random-access memory (RAM), read only memory (ROM), non-volatile RAM (NVRAM), electrically erasable programmable ROM (EEPROM), flash memory, and the like. Memory 126 may store computer-readable instructions that, when executed by processor 124, cause lead detection system 102 to perform various functions. Memory 126 may be a storage device or other non-transitory medium. As shown in FIG. 10, memory 126 may store lead detection module 140 and lead parameters 150.

Lead parameters 150 may include various parameters about leads, such as lead 50. Examples of parameters that may be included in lead parameters 150 include, but are not limited to, such as models of leads (e.g., CAD models, template models, etc.), coordinates of centers of orientation markers and electrodes of the lead, distances between orientation markers and electrodes of the lead, angles between a vector connecting the orientation markers and centers of the electrodes, or any other parameters. In some examples, lead parameters 150 may include respective sets of lead parameters for different models of leads. For instance, lead parameters 150 may include a first set of lead parameters for a first lead model and a second set of lead parameters for a second lead model.

Communication module 142 may communicate with external devices via one or more wired and/or wireless networks by transmitting and/or receiving network signals on the one or more networks. Examples of communication module 142 include a network interface card (e.g. such as an Ethernet card), an optical transceiver, a radio frequency transceiver, a GPS receiver, or any other type of device that can send and/or receive information. Other examples of communication units 142 may include short wave radios, cellular data radios, wireless network radios, as well as universal serial bus (USB) controllers.

In accordance with one or more techniques of this disclosure, lead detection module 140 may be executable by processor 124 to determine a location and/or orientation of a lead implanted in a patient based on image data representing the lead implanted in the patient (e.g., image data generated by an imaging device, such as imaging device 100 of FIG. 1). The image data may represent a relatively small volume of interest containing the lead (e.g., the portion of the lead carrying the electrodes and the orientation markers). In some examples, lead detection module 140 may perform pre-processing on the image data. For instance, lead detection module 140 may use linear interpolation to resample the volume of interest to a fixed voxel resolution (e.g., 0.1 mm×0.1 mm×0.1 mm).

Lead detection module 140 may determine various parameters of the lead. As one example, lead detection system 140 may receive a representation of user input indicating a manufacturer and model of the lead. As another example, lead detection system 140 may receive a message from the IMD indicating a manufacturer and model of the lead (e.g., via a telemetry link). Based on the manufacturer and model, lead detection module 140 may query lead parameters 150 to determine the parameters of the lead.

Lead detection module 140 may analyze the image data to identify centroids of the electrodes and the orientation markers. For instance, lead detection module 140 may select a threshold, and identify the centroids using the selected threshold. In some examples, lead detection module 140 may select the threshold adaptively. For instance, lead detection module 140 may sort all of the intensities of the image and select the Nth highest intensity as the threshold (e.g., such that N=V_Electrodes/One_Voxel_volume, where One_Voxel_Volume is the volume of a single voxel and V_Electrodes (e.g., 3.5 mm$^3$) is the volume of an electrode). As such, lead detection module 140 may select the brightest voxels with a certain fixed volume V_Electrodes as potential electrodes. In some examples, lead detection module 140 may obtain a value for V_Electrodes from lead parameters 150. In other examples, lead detection module 140 may use a fixed value for V_Electrodes for all leads.

Lead detection module 140 may apply the selected threshold to the image data to identify locations of the centroids of the electrodes. For instance, lead detection module 140 may identify connected components of voxels having intensities greater than (or equal to) the threshold, and determine centroids (weighted by image intensity) of each component. Where the lead in the image includes X electrodes, lead detection module 140 may identify X centroids respectively corresponding to the X electrodes. In some examples, lead detection module 140 may generate an error if additional or fewer centroids are identified. For instance, where the lead includes 4 electrodes, lead detection module 140 may generate an error if applying the selected threshold yields more or less than 4 centroids.

Where lead detection module 140 generates an error, lead detection module 140 may output an indication of the error using any suitable technique. For instance, lead detection module 140 may cause output device 144 to display a graphical representation of the error (e.g., an error message).

Lead detection module 140 may identify the centroids using any suitable technique. As one example, lead detection module 140 may identity a centroid of a particular connected component (e.g., electrode or marker) as the voxel corresponding to the arithmetic mean position of all voxels in the connected component.

In some examples, lead detection module 140 may identify initial positions of the centroids and refine the initial positions using various techniques. For instance, based on the assumption that the centroids of the electrodes should be in a line, lead detection module 140 may refine the positions of the centroids to fit a line. As one example, lead detection module 140 may apply singular value decomposition (SVD) to the initial centroids to find a best linear fit and modify the initial positions to fit the identified line.

Lead detection module 140 may identify locations of the orientation markers based on the identified locations of the electrodes. For instance, lead detection module 140 may mask out (e.g., set to zero) the voxels within a certain radius (e.g., 1.0 mm, 1.5 mm, 2.0 mm, 2.5 mm, 3.0 mm, 3.5 mm, etc.) around each electrode centroid. Lead detection module 140 may determine the center of all of the determined centroids (i.e. the mean of their location), and mask out all voxels that are outside a certain ring of distances from this center (e.g., all voxels nearer than 7 mm or farther than 18 mm from the center of all electrodes are masked out). Masking out the voxels may be effective as it is expected the markers should be visible within that ring.

Lead detection module 140 may threshold the remaining visible voxels using an adaptive threshold. As such, lead detection module 140 may select that the brightest voxels with a certain fixed volume V_markers (e.g., 1.4 mm$^3$) as potential markers. In some examples, lead detection module 140 may obtain a value for V_markers from lead parameters 150. In other examples, lead detection module 140 may use a fixed value for V_markers for all leads.

Lead detection module 140 may threshold the image using the markers threshold and identify connected components in the thresholded image. While the lead may include multiple (e.g., two) orientation markers, the markers may appear as a single component at this stage (e.g., due to the proximity of the markers). Lead detection module 140 may identify the largest component by volume. If the volume of the identified largest component is less than a certain value which is expected for two merged markers (e.g., less than 1.3 mm$^3$), lead detection module 140 may add the component with the next largest volume is to the first component (e.g., based on an assumption that the next largest volume is a second marker). Lead detection module 140 may identify the (intensity weighted) centroid of the identified component.

After performing the above techniques, lead detection module 140 may have identified linear fit to the electrodes centroids but may not have identified which electrodes are more proximal and which are more distal. Lead detection module 140 may determine (e.g., based on lead parameters 150) that the orientation markers should be closer to the proximal electrode (e.g., electrode 68 of FIG. 3). To identify which electrodes are more proximal and which are more distal, lead detection module 140 may project the centroids of the electrodes on a vector representing the electrodes fitted line. This projection may result in a single number being assigned to each electrode. Lead detection module 140 may project the centroids of the orientation markers onto the same line, yielding another number. If the markers projection is not greater than all the electrode projections, lead detection module 140 may reverse the direction of the line fit vector. As such, lead detection module 140 may assure that the vector points from the most distal electrode (e.g., electrode 62 of FIG. 3) towards the most proximal electrode (e.g., electrode 68 of FIG. 3).

Lead detection module 140 may determine a rotation matrix that would rotate the electrodes line fit vector into a particular axis (e.g., a "z axis"), pointing toward a positive direction of the particular axis. In some examples, lead detection module 140 may use Rodrigues' rotation formula to compute the rotation matrix while treating edge cases of gimbal lock.

Lead detection module 140 may rotate the coordinate system of the markers component according to the rotation matrix found above. Lead detection module 140 may apply a translation that puts the origin at the center of the markers. As such, it may be assumed that the voxels with most positive coordinate in the particular axis (e.g., most positive coordinate in the z axis) to belong to one marker, and the voxels with most negative coordinate in the particular axis (e.g., most negative coordinate in the z axis) to belong to a second marker. Specifically, lead detection module 140 may identify all voxels having coordinates in the particular axis greater than a threshold distance (e.g., D) as a first marker (e.g., marker 82A of FIG. 3) and identify all voxels having coordinates in the particular axis less than a negative of the threshold distance (e.g., –D) as a second marker (e.g., marker 82B of FIG. 3). For instance, lead detection module 140 may identify the first marker as all voxels with z>D, and identify the second marker as all voxels with z<–D, where D is a certain distance from the center of the markers, such as 0.41 mm.

Lead detection module 140 may identify the centroids (intensity weighted) of each of the markers. For instance, lead detection module 140 may identify a centroid of the voxels identified as the first marker and identify a centroid of the voxels identified as the second marker.

Lead detection module 140 may utilize any combination of the identified centroids of the electrodes, the identified centroids of the orientation markers, and the identified fit line/vector direction to determine the orientation of the lead. As discussed above, lead detection module 140 may utilize a first technique involving determining a vector between projections of the centroids of the markers, a second technique involving template matching the identified centroids, or a combination of the first technique and the second technique.

To determine the orientation of the lead using the first technique, lead detection module 140 may determine a plane (e.g., plane 86 of FIG. 5) orthogonal to the identified fit line. As this identified fit line represents longitudinal axis 70 (i.e., the electrode axis), the determined plane may be approximately orthogonal to longitudinal axis 70.

Lead detection module 140 may project the identified centroids of the orientation markers into the determined plane. For instance, as shown in FIG. 5, lead detection module 140 may project the locations of centroids 82A' and 82B' (respectively corresponding to the locations of orientation markers 82A and 82B) into plane 86 as projected centroids 82A" and 82B".

Lead detection module 140 may determine a vector that connects the first marker to the second marker. For instance, as shown in FIG. 5, lead detection module 140 may calculate vector 84 that connects projected centroids 82A" and 82B" in plane 86. Vector 84 may represent the rotational orientation of orientation markers 82, and thus the rotational orientation of lead 50. In this way, lead detection module 140 may determine the rotational orientation of the lead.

In some examples, lead detection module 140 may determine the rotational orientation of various electrodes of the lead (e.g., in one or both of an image coordinate system of a patient coordinate system). For instance, lead detection module 140 may obtain various offset angles from lead parameters 150. The offset angles may represent angular offsets between the vector between the orientation markers and various electrode segments. As one example, lead detection module 140 may obtain a first angle that represent an offset between the vector between the orientation markers and a center of a first electrode segment (e.g., an angle between orientation markers 82A and 82B, and electrode segment 66A of FIG. 3), a second angle that represent an offset between the vector between the orientation markers and a center of a second electrode segment (e.g., an angle between orientation markers 82A and 82B, and electrode segment 66B of FIG. 3), . . . , and an nth angle that represent an offset between the vector between the orientation markers and a center of an nth electrode segment. Lead detection module 140 may utilize the offset angles to determine various vectors, which may be perpendicular to longitudinal axis 70, that represent the directions in which the directional electrodes are pointing.

To determine the orientation of the lead using the second technique, lead detection module 140 may obtain a pre-determined template of expected centroids the electrodes of the lead in the image. The pre-determined template may be in a fixed, lead based, coordinate system. Lead detection module 140 may determine a transform between the centroids determined from the image and the centroids in the template. For instance, lead detection module 140 may use SVD to determine a best fit rigid transform between the centroids in the template and corresponding centroids 82A', 82B', 62', 64', 66', and 68'. Based on the determined transform, lead detection module 140 may determine the orientation of the lead.

Similar to the first technique, the obtained template may indicate respective angles of each of the electrode segments. As such, based on the determined transform, lead detection module 140 may determine various vectors, which may be perpendicular to longitudinal axis 70, that represent the directions in which the directional electrodes are pointing.

Regardless of the particular technique utilized, lead detection module 140 may generate an output that includes any combination of the following: the centroid of distal electrode (3D point) in voxel coordinates, the direction of lead trajectory (from distal electrode towards proximal electrode (3D vector)), the direction of the center of a target electrode segment (3D vector, perpendicular to the direction of the lead trajectory), a confidence score (e.g., a value representing the likelihood that the other outputs are accurate), and one or more error codes.

Lead detection module 140 may provide the output via any channel. As one example, lead detection module 140 may cause output device 144 to display a graphical representation of the lead overlaid on an image of the patient in which the lead is implanted. The graphical representation may show the orientation and/or location of the lead relative to the patient (e.g., relative to one or more anatomical structures of the patient). As another example, lead detection module 140 may cause output device 144 to display numerical representations of any combination of the outputs described above (e.g., centroid of distal electrode, direction of lead trajectory, direction of the center of the target electrode segment).

Figure 11:
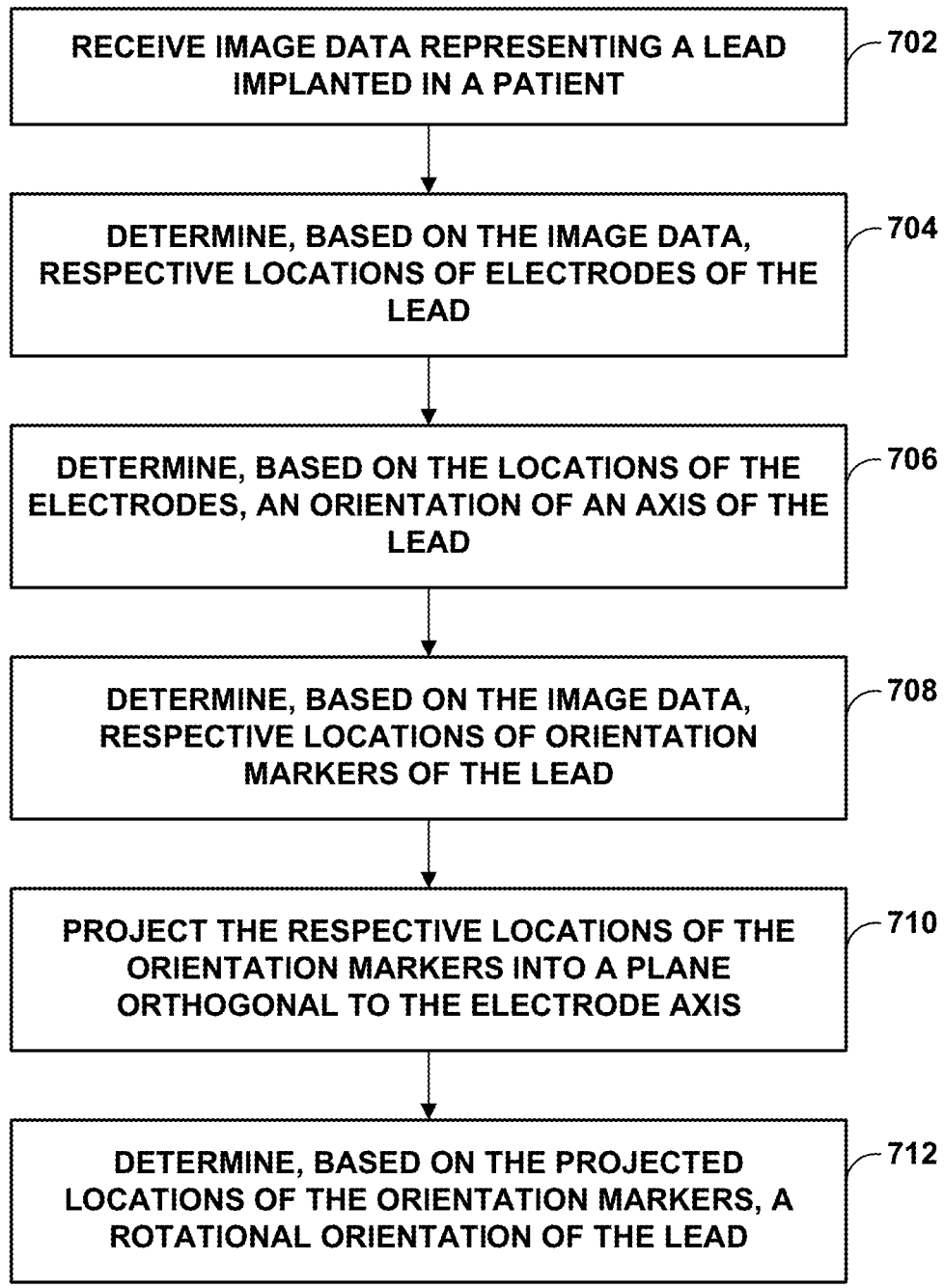
FIG. 11 is a flow diagram illustrating an example technique for determining the orientation of a lead implanted in a patient, in accordance with one or more techniques of this disclosure.

FIG. 11 is a flow diagram illustrating an example technique for determining the orientation of a lead implanted in a patient, in accordance with one or more techniques of this disclosure. For purposes of explanation, the technique of FIG. 11 will be described with respect to lead detection system 102 of FIGS. 1 and 6. However, lead detection systems other than lead detection system 102 may perform some or all of the technique of FIG. 11.

Lead detection system 102 may obtain image data representing a lead implanted in a patient (702). For instance, communication module 142 of lead detection system 102 may obtain, from imaging device 100, computed tomography (CT) images of patient 40 of FIG. 1 of a region of patient 40 in which lead 50 is implanted. As discussed above, example formats of the image data include, but are not necessarily limited to, Analyze, Neuroimaging Informatics Technology Initiative (Nifti), Minc, and Digital Imaging and Communications in Medicine (Dicom).

Lead detection system 102 may determine, based on the image data, respective locations of electrodes of the lead (704). For instance, lead detection module 140 may be executable by processor 124 to adaptively determine a threshold (e.g., based on a known quantity of electrodes included in the lead, and a known volume of the electrodes), apply the determined threshold to the image data, identify connected components in the thresholded image data, and identify centroids of the connected components. The centroids of the connected components representing the locations of the electrodes.

Lead detection system 102 may determine, based on the locations of the electrodes, an orientation of an axis of the lead (706). For instance, lead detection module 140 may be executable by processor 124 to determine (e.g., using SVD) a linear fit line to fit the identified centroids. As discussed above, the axis of the lead may correspond to longitudinal axis 70 of lead 50 of FIG. 3.

Lead detection system 102 may determine, based on the image data, respective locations of orientation markers of the lead (708). For instance, lead detection module 140 may be executable by processor 124 to mask out (e.g., set to zero) voxels in the image data that correspond to the electrodes, adaptively determine a threshold (e.g., based on a known volume of the markers), apply the determined threshold to the image data, identify connected components in the thresholded image data, and identify centroids of the connected components. The centroids of the connected components representing the locations of the orientation markers.

Lead detection system 102 may project the respective locations of the orientation markers into a plane orthogonal to the longitudinal axis (710). For instance, lead detection module 140 may be executable by processor 124 to calculate the plane (e.g., plane 86 of FIG. 5), and project locations of orientation markers 82A' and 82B' into the plane to obtain projected locations 82A" and 82B" of FIG. 4.

Lead detection system 102 may determine, based on the projected locations of the orientation markers, a rotational orientation of the lead (712). For instance, lead detection module 140 may be executable by processor 124 to calculate a vector (e.g., vector 84 of FIG. 5) pointing from a first marker of the orientation markers to a second marker of the orientation markers. As discussed above, vector 84 may represent the rotational orientation of orientation markers 82, and thus the rotational orientation of lead 50.

Lead detection system 102 may output an indication of the determined rotational orientation. For instance, lead detection module 140 may be executable by processor 124 to cause output device 144 to display a graphical representation of the lead overlaid on an image of the patient in which the lead is implanted. The graphical representation may show the orientation and/or location of the lead relative to the patient. As another example, lead detection module 140 may cause output device 144 to display numerical representations of any combination of the outputs described above (e.g., centroid of distal electrode, direction of lead trajectory, direction of the center of the target electrode segment).

A practitioner may utilize the determined rotational orientation of the lead to program (e.g., using programmer 30) operation of IMD 20. As one example, where it is desirable to deliver electrical stimulation therapy to a particular volume of the patient's brain (e.g., a specific volume of activation), the practitioner may use programmer 30 to program IMD 30 to deliver electrical stimulation therapy via electrodes of lead 50 that activate the particular volume.

Figure 12:
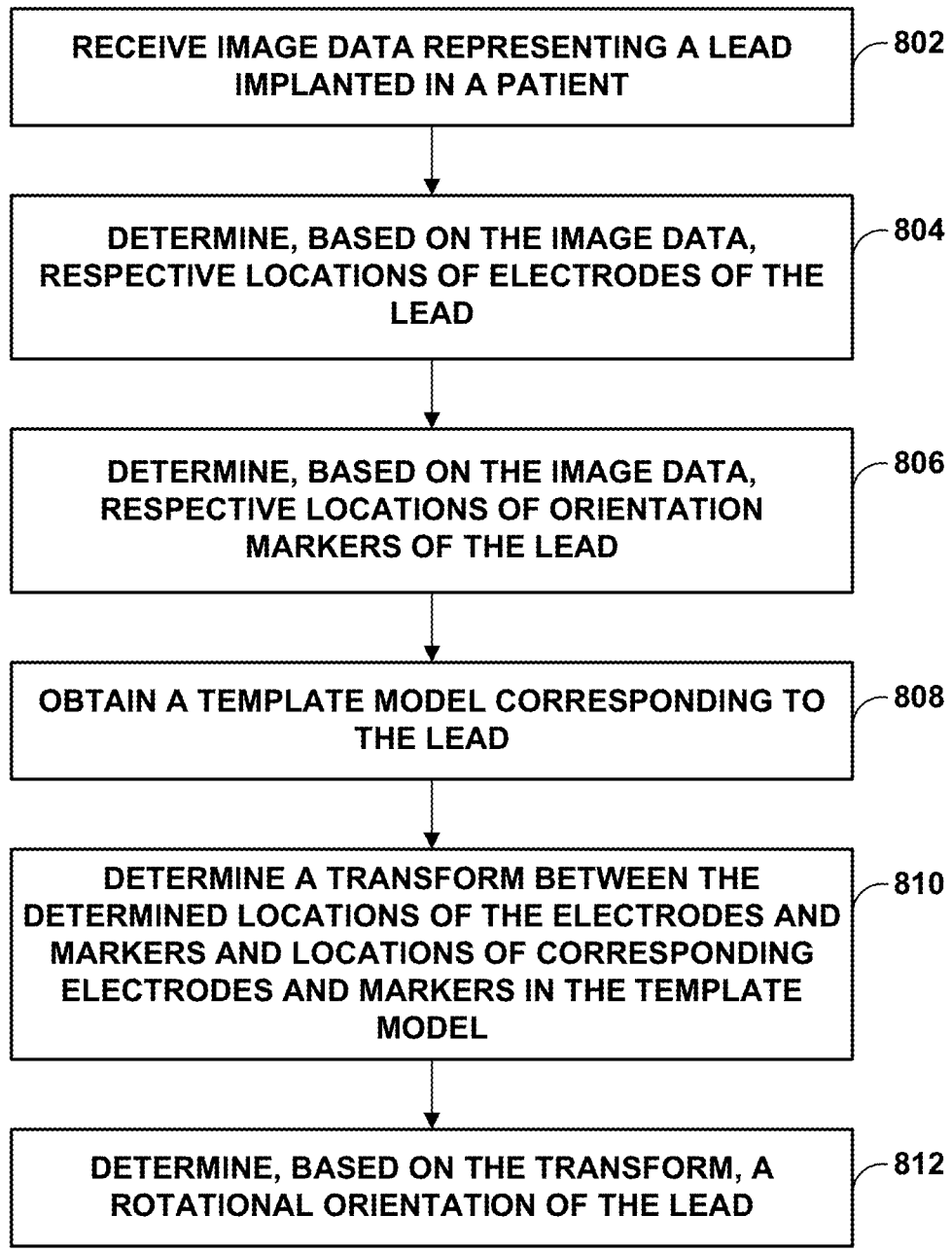
FIG. 12 is a flow diagram illustrating another example technique for determining the orientation of a lead implanted in a patient, in accordance with one or more techniques of this disclosure.

FIG. 12 is a flow diagram illustrating another example technique for determining the orientation of a lead implanted in a patient, in accordance with one or more techniques of this disclosure. For purposes of explanation, the technique of FIG. 12 will be described with respect to lead detection system 102 of FIGS. 1 and 6. However, lead detection systems other than lead detection system 102 may perform some or all of the technique of FIG. 12.

Lead detection system 102 may obtain image data representing a lead implanted in a patient (802). For instance, communication module 142 of lead detection system 102 may obtain, from imaging device 100, computed tomography (CT) images of patient 40 of FIG. 1 of a region of patient 40 in which lead 50 is implanted. As discussed above, example formats of the image data include, but are not necessarily limited to, Analyze, Neuroimaging Informatics Technology Initiative (Nifti), Minc, and Digital Imaging and Communications in Medicine (Dicom).

Lead detection system 102 may determine, based on the image data, respective locations of electrodes of the lead (804). For instance, lead detection module 140 may be executable by processor 124 to adaptively determine a threshold (e.g., based on a known quantity of electrodes included in the lead, and a known volume of the electrodes), apply the determined threshold to the image data, identify connected components in the thresholded image data, and identify centroids of the connected components. The centroids of the connected components representing the locations of the electrodes.

Lead detection system 102 may determine, based on the image data, respective locations of orientation markers of the lead (806). For instance, lead detection module 140 may be executable by processor 124 to mask out (e.g., set to zero) voxels in the image data that correspond to the electrodes, adaptively determine a threshold (e.g., based on a known volume of the markers), apply the determined threshold to the image data, identify connected components in the thresholded image data, and identify centroids of the connected components. The centroids of the connected components representing the locations of the orientation markers.

Lead detection system 102 may obtain a template model corresponding to the lead (808). For instance, lead detection module 140 may be executable by processor 124 to obtain, from lead parameters 150, a template model, in a fixed lead based coordinate system, of a lead corresponding to the lead implanted in the patient.

Lead detection system 102 may determine a transform between the determined locations of the electrodes and markers and locations of corresponding electrodes and markers in the template model (810). For instance, lead detection module 140 may be executable by processor 124 to calculate a three dimensional rotation matrix that transforms the lead in the image data to the lead in the template model. In particular, lead detection module 140 may calculate a 6-parameter 3-D rigid body transform between the identified centroids of the electrodes and markers and centroids of corresponding electrodes and markers in the template model.

Lead detection system 102 may determine, based on the transform, a rotational orientation of the lead (812). For instance, lead detection module 140 may be executable by processor 124 to identify the rotational orientation of the lead based on the Euler angle yaw in the transform around the lead axis, with lead-axis along the z-axis (e.g., longitudinal axis 70) in the lead coordinates system.

Lead detection system 102 may output an indication of the determined rotational orientation. For instance, lead detection module 140 may be executable by processor 124 to cause output device 144 to display a graphical representation of the lead overlaid on an image of the patient in which the lead is implanted. The graphical representation may show the orientation and/or location of the lead relative to the patient. As another example, lead detection module 140 may cause output device 144 to display numerical representations of any combination of the outputs described above (e.g., centroid of distal electrode, direction of lead trajectory, direction of the center of the target electrode segment).

A practitioner may utilize the determined rotational orientation of the lead to program (e.g., using programmer 30) operation of IMD 20. For instance, where it is desirable to deliver electrical stimulation therapy to a particular volume of the patient's brain (e.g., a specific volume of activation), the practitioner may use programmer 30 to program IMD 30 to deliver electrical stimulation therapy via electrodes of lead 50 that activate the particular volume.

While the techniques described above are primarily described as being performed by processor 124 of lead detection system 102, in other examples, one or more other processors may perform any part of the techniques described herein alone or in addition to processor 124. Thus, reference to "a processor" may refer to "one or more processors." Likewise, "one or more processors" may refer to a single processor or multiple processors in different examples.

The techniques described in this disclosure, including those attributed to lead detection system 102 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The following numbered examples may illustrate one or more aspects of this disclosure:

Example 1

A method comprising: obtaining an image of a lead implanted in a patient, the lead including one or more electrodes positioned along a longitudinal axis of the lead and a plurality of orientation markers; determining, in the image, respective locations of the one or more electrodes and respective locations of the plurality of orientation markers; determining, based on the respective locations of the one or more electrodes, an orientation of the longitudinal axis; projecting the respective locations of the orientation markers into a plane orthogonal to the longitudinal axis; and determining, based on a projected location of a first orientation marker of the plurality of orientation markers in the plane and a projected location of a second orientation marker of the plurality of orientation markers in the plane, a rotational orientation of the lead.

Example 2

The method of example 1, wherein determining the respective locations of the electrodes and the respective locations of the orientation markers comprises determining respective locations of centroids of the electrodes and respective locations of centroids of the orientation markers.

Example 3

The method of any of examples 1 or 2, wherein the one or more electrodes comprise a plurality of electrodes positioned at different angular positions around the longitudinal axis.

Example 4

The method of any combination of examples 1-3, further comprising: identifying, in the image, the first orientation marker and the second orientation marker, wherein determining the rotational orientation of the lead comprises: determining a vector connecting the first orientation marker and the second orientation marker; and determining the rotational orientation of the lead based on the vector.

Example 5

The method of example 4, further comprising: obtaining a pre-determined offset angle between the vector and an electrode of the one or more electrodes; and adding the pre-determined offset angle to the determined vector to determine a rotational orientation of the electrode.

Example 6

The method of any combination of examples 1-5, wherein determining the orientation of the longitudinal axis comprises: determining a best fit line based on the determined locations of the electrodes.

Example 7

The method of any combination of examples 1-6, wherein the lead comprises a segmented lead, and the one or more electrodes are configured to deliver electrical stimulation therapy.

Example 8

The method of any combination of examples 1-7, further comprising: determining a quantity of electrodes included in the one or more electrodes; determining a quantity of the determined locations of the one or more electrodes; determining that the quantity of the determined locations of the one or more electrodes is different than the quantity of the electrodes; and responsive to determining that the quantity of the determined locations is different than the quantity of electrodes included in the one or more electrodes, outputting an error.

Example 9

The method of any combination of examples 1-8, further comprising: obtaining a template model of the lead; and determining a transform between the determined locations of the one or more electrodes and the plurality of the orientation markers and locations of corresponding electrodes and orientation markers in the template model, wherein determining the rotational orientation of the lead further comprises: determining the rotational orientation of the lead based on the transform.

Example 10

A system comprising: a memory; and processing circuitry configured to perform the method of any combination of examples 1-9.

Example 11

A system comprising means for performing the method of any combination of examples 1-9.

Example 12

A computer-readable storage medium storing instructions that, when executed, cause one or more processors to perform the method of any combination of examples 1-9.

Example 13

A method comprising: obtaining an image of a lead implanted in a patient, the lead including one or more electrodes positioned along a longitudinal axis of the lead and a plurality of orientation markers; determining, in the image, respective locations of the electrodes and respective locations of the orientation markers; obtaining a template model corresponding to the lead; determining a transform between the determined locations of the one or more electrodes and the plurality of orientation markers and locations of corresponding electrodes and orientation markers in the template model; and determining the rotational orientation of the lead based on the transform.

Example 14

The method of example 13, wherein determining the respective locations of the electrodes and the respective locations of the orientation markers comprises determining respective locations of centroids of the electrodes and respective locations of centroids of the orientation markers.

Example 15

The method of any of examples 13 or 14, wherein the one or more electrodes comprise a plurality of electrodes positioned at different angular positions around the longitudinal axis.

Example 16

The method of any combination of examples 13-15, wherein the lead comprises a segmented lead, and the one or more electrodes are configured to deliver electrical stimulation therapy.

Example 17

The method of any combination of examples 13-16, further comprising: determining an orientation of the longitudinal axis.

Example 18

The method of example 17, further comprising: projecting the respective locations of the orientation markers into a plane orthogonal to the longitudinal axis, wherein determining the rotational orientation of the lead further comprises: determining, based on a projected location of a first orientation marker of the plurality of orientation markers in the plane and a projected location of a second orientation marker of the plurality of orientation markers in the plane, the rotational orientation of the lead.

Example 19

The method of example 18, further comprising: identifying, in the image, the first orientation marker and the second orientation marker, wherein determining the rotational orientation of the lead comprises: determining a vector connecting the first orientation marker and the second orientation marker; and determining the rotational orientation of the lead based on the vector.

Example 20

The method of example 19, further comprising: obtaining a pre-determined offset angle between the vector and an electrode of the one or more electrodes; and adding the pre-determined offset angle to the determined vector to determine a rotational orientation of the electrode.

Example 21

The method of any combination of examples 13-20, wherein determining the orientation of the longitudinal axis comprises: determining a best fit line based on the determined locations of the one or more electrodes.

Example 22

A system comprising: a memory; and processing circuitry configured to perform the method of any combination of examples 13-21.

Example 23

A system comprising means for performing the method of any combination of examples 13-21.

Example 24

A computer-readable storage medium storing instructions that, when executed, cause one or more processors to perform the method of any combination of examples 13-21.

Various examples of the disclosure have been described. These and other embodiments are within the scope of the following claims.

What is claimed is:

1. A method comprising:
   obtaining an image of a lead implanted in a patient, the lead including one or more electrodes positioned along a longitudinal axis of the lead and a plurality of orientation markers;
   determining, in the image, respective locations of the electrodes and respective locations of the orientation markers;
   obtaining a template model corresponding to the lead;
   determining a transform between the determined locations of the one or more electrodes and the plurality of orientation markers and locations of corresponding electrodes and orientation markers in the template model; and
   determining the rotational orientation of the lead based on the transform.

2. The method of claim 1, wherein determining the respective locations of the electrodes and the respective locations of the orientation markers comprises determining respective locations of centroids of the electrodes and respective locations of centroids of the orientation markers.

3. The method of claim 1, wherein the one or more electrodes comprise a plurality of electrodes positioned at different angular positions around the longitudinal axis.

4. The method of claim 1, wherein the lead comprises a segmented lead, and the one or more electrodes are configured to deliver electrical stimulation therapy.

5. The method of claim 1, further comprising:
   determining an orientation of the longitudinal axis.

6. The method of claim 5, further comprising:
   projecting the respective locations of the orientation markers into a plane orthogonal to the longitudinal axis, wherein determining the rotational orientation of the lead further comprises:
   determining, based on a projected location of a first orientation marker of the plurality of orientation markers in the plane and a projected location of a second orientation marker of the plurality of orientation markers in the plane, the rotational orientation of the lead.

7. The method of claim 6, further comprising:
   identifying, in the image, the first orientation marker and the second orientation marker, wherein determining the rotational orientation of the lead comprises:
   determining a vector connecting the first orientation marker and the second orientation marker; and
   determining the rotational orientation of the lead based on the vector.

8. The method of claim 7, further comprising:
   obtaining a pre-determined offset angle between the vector and an electrode of the one or more electrodes; and
   adding the pre-determined offset angle to the determined vector to determine a rotational orientation of the electrode.

9. The method of claim 5, wherein determining the orientation of the longitudinal axis comprises:
   determining a best fit line based on the determined locations of the one or more electrodes.

10. A system comprising:
    a memory; and
    processing circuitry configured to:
      obtain an image of a lead implanted in a patient, the lead including one or more electrodes positioned along a longitudinal axis of the lead and a plurality of orientation markers;
      determine, in the image, respective locations of the electrodes and respective locations of the orientation markers;
      obtain a template model corresponding to the lead;
      determine a transform between the determined locations of the one or more electrodes and the plurality of orientation markers and locations of corresponding electrodes and orientation markers in the template model; and
      determine the rotational orientation of the lead based on the transform.

11. The system of claim 10, wherein, to determine the respective locations of the electrodes and the respective locations of the orientation markers, the processing circuitry is configured to determine respective locations of centroids of the electrodes and respective locations of centroids of the orientation markers.

12. The system of claim 10, wherein the one or more electrodes comprise a plurality of electrodes positioned at different angular positions around the longitudinal axis.

13. The system of claim 10, wherein the lead comprises a segmented lead, and the one or more electrodes are configured to deliver electrical stimulation therapy.

14. The system of claim 10, wherein the processing circuitry is further configured to determine an orientation of the longitudinal axis.

15. The system of claim 14, wherein the processing circuitry is further configured to:
project the respective locations of the orientation markers into a plane orthogonal to the longitudinal axis, wherein, to determine the rotational orientation of the lead, the processing circuitry is configured to:
determine, based on a projected location of a first orientation marker of the plurality of orientation markers in the plane and a projected location of a second orientation marker of the plurality of orientation markers in the plane, the rotational orientation of the lead.

16. The system of claim 15, wherein the processing circuitry is further configured to:
identify, in the image, the first orientation marker and the second orientation marker, wherein, to determine the rotational orientation of the lead, the processing circuitry is configured to:
determine a vector connecting the first orientation marker and the second orientation marker; and
determine the rotational orientation of the lead based on the vector.

17. The system of claim 16, wherein the processing circuitry is further configured to:
obtain a pre-determined offset angle between the vector and an electrode of the one or more electrodes; and
add the pre-determined offset angle to the determined vector to determine a rotational orientation of the electrode.

18. The system of claim 14, wherein, to determine the orientation of the longitudinal axis, the processing circuitry is configured to determine a best fit line based on the determined locations of the one or more electrodes.

19. A non-transitory computer-readable storage medium storing instructions that, when executed, cause one or more processors to:
obtain an image of a lead implanted in a patient, the lead including one or more electrodes positioned along a longitudinal axis of the lead and a plurality of orientation markers;
determine, in the image, respective locations of the electrodes and respective locations of the orientation markers;
obtain a template model corresponding to the lead;
determine a transform between the determined locations of the one or more electrodes and the plurality of orientation markers and locations of corresponding electrodes and orientation markers in the template model; and
determine the rotational orientation of the lead based on the transform.

20. The non-transitory computer-readable storage medium of claim 19, wherein:
the instructions that cause the one or more processors to determine the respective locations of the electrodes and the respective locations of the orientation markers comprise instructions that cause the one or more processors to determine respective locations of centroids of the electrodes and respective locations of centroids of the orientation markers,
the one or more electrodes comprise a plurality of electrodes positioned at different angular positions around the longitudinal axis, and
the lead comprises a segmented lead, and the one or more electrodes are configured to deliver electrical stimulation therapy.

* * * * *